US011054415B2

(12) United States Patent
Abad Fuentes et al.

(10) Patent No.: US 11,054,415 B2
(45) Date of Patent: Jul. 6, 2021

(54) PREPARATION OF BIOCONJUGATES AND ANTIBODIES FOR THE IMMUNODETECTION OF ANATOXIN-A

(71) Applicants: CONSEJO SUPERIOR DE INVESTIGACIONES CIENTIFICAS, Madrid (ES); UNIVERSITAT DE VALÈNCIA, Valencia (ES)

(72) Inventors: Antonio Abad Fuentes, Valencia (ES); Josep Vicent Mercader Badia, Valencia (ES); Antonio Abad Somovilla, Valencia (ES); Consuelo Agulló Blanes, Valencia (ES); Guillermo Quiñones Reyes, Valencia (ES)

(73) Assignees: CONSEJO SUPERIOR DE INVESTIGACIONES CIENTIFICAS, Madrid (ES); UNIVERSITAT DE VALÈNCIA, Valencia (ES)

( * ) Notice: Subject to any disclaimer, the term of this patent is extended or adjusted under 35 U.S.C. 154(b) by 457 days.

(21) Appl. No.: 15/776,814

(22) PCT Filed: Sep. 21, 2016

(86) PCT No.: PCT/ES2016/070656
§ 371 (c)(1),
(2) Date: Sep. 17, 2018

(87) PCT Pub. No.: WO2017/085339
PCT Pub. Date: May 26, 2017

(65) Prior Publication Data
US 2019/0265233 A1 Aug. 29, 2019

(30) Foreign Application Priority Data
Nov. 17, 2015 (ES) .............. ES201531661

(51) Int. Cl.
*G01N 33/532* (2006.01)
*C07D 487/08* (2006.01)
*C07K 16/12* (2006.01)
*B01D 15/38* (2006.01)
*G01N 33/531* (2006.01)

(52) U.S. Cl.
CPC ....... *G01N 33/532* (2013.01); *B01D 15/3809* (2013.01); *C07D 487/08* (2013.01); *C07K 16/12* (2013.01); *G01N 33/531* (2013.01); *C07K 2317/76* (2013.01); *C07K 2317/92* (2013.01)

(58) Field of Classification Search
CPC .. A61K 2039/55566; A61K 2039/6081; A61K 39/385; B01D 15/3809; C07D 487/08; C07K 16/12; C07K 16/44; C07K 2317/33; C07K 2317/76; C07K 2317/92; G01N 33/531; G01N 33/532
See application file for complete search history.

(56) References Cited

U.S. PATENT DOCUMENTS

2012/0088312 A1* 4/2012 Salamone ............ C07D 519/04
436/501

OTHER PUBLICATIONS

Huby et al., "Structural modification of anatoxin-a. Synthesis of model affinity ligands for the nicotinic acetylcholine receptor," J. Chem. Soc., Chem. Commun., 1991, issue 4, pp. 243-245.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Araoz et al., "Neurotoxic cyanobacterial toxins", Elsevier, Toxicon, vol. 56, Issue 5, Oct. 2010, pp. 813-828, 16 pages.
Pegram et al., "Chapter 15: Cyanotoxins Workgroup Report", "Advances in experimental medicine and biology", vol. 619, 2008, pp. 317-381, 2008, 66 pages.
Gutierrez-Praena et al., "Presence and bioaccumulation of microcystins and cylindrospermopsin in food and the effectiveness of some cooking techniques at decreasing their concentrations: a review", Elsevier, Food and Chemical Toxicology, vol. 53, pp. 139-152, 2013, 14 pages.
Kanne et al., "Synthesis of the First Highly Potent Bridged Nicotinoid. 9-Azabicyclo[4.2.1]nona[2,3-c]pyridine (pyrido[3,4-b]homotropane)", Journal of American Chemical Society, 1986 vol. 108 (24), 7864-7865, 2 pages.
Lemoine et al., "Ultra-fast analysis of anatoxin-A using laser diode thermal desorption-atmospheric pressure chemical ionization—tandem mass spectrometry: Validation and resolution from phenylalanine", Elsevier, Toxicon, vol. 61, Jan. 2013, pp. 165-174, 10 pages.
Marc et al., "Synthesis of a (+)-anatoxin-a analogue for monoclonal antibodies production", Elsevier, Tetrahedron Letters, vol. 50, Issue 31, Aug. 5, 2009, pp. 4554-4557, 4 pages.
Osswald et al., "Toxicology and detection methods of the alkaloid neurotoxin produced by cyanobacteria, anatoxin-a", Elsevier, Environment International, vol. 33, 2007, pp. 1070-1089, 20 pages.
Roy-Lachapelle et al., "High resolution/accurate mass (HRMS) detection of anatoxin-a in lake water using LDTD-APCI coupled to a Q-Exactive mass spectrometer", Elsevier, Talanta, vol. 132, 2015, pp. 836-844, 9 pages.

* cited by examiner

*Primary Examiner* — Galina M. Yakovleva
(74) *Attorney, Agent, or Firm* — Hayes Soloway PC

(57) ABSTRACT

The present invention relates to bioconjugates and labeled derivatives of anatoxin-a, at different positions of the molecule, suitable for producing antibodies with high affinity and specificity for anatoxin-a. At the same time, the present invention also relates to the use of bioconjugates of anatoxin-a and labeled derivatives of anatoxin-a as assay antigens. Moreover, the present invention also relates to methods for analyzing, concentrating and extracting anatoxin-a using the antibodies obtained, sometimes together with assay antigens which are bioconjugates or labeled derivatives. This invention also provides a kit for analyzing anatoxin-a which comprises antibodies against this cyanotoxin sometimes together with assay antigens which are bioconjugates or labeled derivatives of anatoxin-a.

2 Claims, 5 Drawing Sheets

PREPARATION OF BIOCONJUGATES AND ANTIBODIES FOR THE IMMUNODETECTION OF ANATOXIN-A

The present invention relates to bioconjugates and labeled derivatives of anatoxin-a, at different positions of the molecule, suitable for producing antibodies with high affinity and specificity for anatoxin-a. At the same time, the present invention also relates to the use of bioconjugates of anatoxin-a and labeled derivatives of anatoxin-a as assay antigens. Moreover, the present invention also relates to methods for analyzing, concentrating and extracting anatoxin-a using the antibodies obtained, sometimes together with assay antigens which are bioconjugates or labeled derivatives. This invention also provides a kit for analyzing anatoxin-a which comprises antibodies against this cyanotoxin sometimes together with assay antigens which are bioconjugates or labeled derivatives of anatoxin-a.

STATE OF THE ART

Biotoxins are a type of contaminant whose presence in foodstuffs, water and animal feeds means a real problem for human health and animal wellbeing, causing significant economic losses to the agri-food, agricultural and fishing sectors and may seriously affect the safety of drinking water. The most relevant biotoxins, due to their toxicity and prevalence, include those produced by cyanobacteria, especially microcystin-LR, cylindrospermopsin and anatoxin-a.

Anatoxin-a (2-acetyl-9-azabicyclo[4.2.1]non-2-ene] is a bicyclic secondary amine which incorporates an alpha, beta unsaturated methyl carbonyl residue Anatoxin-a This toxin is produced by different cyanobacteria species belonging fundamentally to the genera, *Anabaena, Microcystis, Aphanizomenon, Oscillatoria, Planktothrix* and *Cylindrosperum*. Under certain environmental conditions, these prokaryote microorganisms are capable of proliferating in an exacerbated manner, producing sudden eclosions, known in scientific literature as massive algae blooms [Osswald et al., Environ. Int., 2007, 33, 1070-1089]. These blooms are currently considered more frequent and intense than in the past due to the eutrophication as a result of human activity and global warming [Taranu et al., *Ecol. Lett.*, 2015, 18, 375-384]. The main exposure routes of the human and animal population to anatoxin-a are through contaminated water, whether it is ingested intentionally (drinking water coming from surface sources) or accidentally (recreational and sport uses) and through the consumption of dietary supplements derived from algae which do not always have suitable checks and which may therefore contain undesired cyanobacteria species that produce toxins [Gutiérrez-Praena et al., *Food Chem. Toxicol.*, 2013, 53, 139-152]. One exposure route which has gained greater relevance in recent years and which therefore constitutes an emerging risk is through the consumption of fish and bivalve mollusks originating both from traditional fishing and fish farming which have been developed in water bodies affected by cyanobacteria blooms and which therefore have been exposed to these biotoxins [Ibelings et al., *Environ. Pollut.*, 2007, 150, 177-192; Miller et al., *PLOS ONE*, 2010, 5, e12576;].

The first confirmed case of intoxication due to anatoxin-a occurred in Canada in the 1960s where it caused the death of cattle and at that time, due to the high toxicity thereof, was termed Very Fast Death Factor—intraperitoneally injected into mice, animalsdied in less than 5 minutes [Aráoz et al., *Toxicon*, 2010, 56, 813-828; Osswald et al., *Environ. Int.*, 2007, 33, 1070-1089]. Its high potency as a neurotoxin ($LD_{50}$ intraperitoneal in mice: 250 µg/kg) is due to the fact that it is an agonist of acetylcholine, irreversibly binding to the nicotinic acetylcholine receptor at the neuromuscular level blocking the sodium channel and preventing the repolarization of the membrane, thus producing muscular overstimulation which causes convulsions, paralysis and ultimately death due to cardiorespiratory arrest. Anatoxin-a is one of the most frequently detected cyanotoxins which, together with toxicology and epidemiology criteria, has led to the US Environmental Protection Agency (USEPA) to consider it a priority contaminant and to encourage additional studies on risk evaluation that eventually allow setting up regulations and directives on this issue [Hudnell and Dortch, In *Cyanobacterial Harmful Algal Blooms* (Chapter 2), Ed. H. K. Hudnell, Springer, N.Y., USA. 2008]. In line with this concern, the EFSA recently advised to consider the possible presence of cyanotoxins in foodstuffs as an emerging risk and published a call for tender to review the literature on cyanobacteria toxins in food (OC/EFSA/SCER/2014/04).

A large number of fatal cases have been recorded due to intoxication by anatoxin-a in domestic animals, cattle and wildlife as a result of the intake of contaminated water, where concentrations greater than 1 mg/l have been found, a value at least 100 times greater than the maximum concentration considered safe by different official bodies [Trainer et al., *Toxins*, 2015, 7, 1206-1234]. In many geographical areas the problem is recurrent and incidents are recorded every year.

In accordance with a contaminant that is so widely distributed and relevant, various methods have been developed for its detection [Dimitrakopoulos et al., *Anal. Bioanal. Chem.*, 2010, 397, 2245-2252; Lemoine et al., *Toxicon*, 2013, 61, 164-174; Roy-Lachapelle et al., *Talanta*, 2015, 132, 836-844], although the HPLC MS/MS technique is without doubt the most sensitive and widely acceptable method, and it is used by the USEPA as the official method for the determination of anatoxin-a. However, there is broad consensus regarding the need to obtain antibodies against anatoxin-a and to develop fast and reliable analytical methods which allow to effectively manage the crises that may arise, preventing damage to human health and to ecosystems. As early as 2005 in a symposium on cyanotoxins, the development of an ELISA for anatoxin-a was identified as a priority research topic, an objective which is still valid 10 years later [Pegram and Nichols, In *Cyanobacterial Harmful Algal Blooms* (Chapter 15), Ed. H. K. Hudnell, Springer, N.Y., USA. 2008]. The more similar procedure to an immunoanalytical method developed so far is a test based on the use of the acetylcholine receptor originating from electrocyte membranes of the electric ray (Torpedo sp.) [Aráoz et al., *Toxicon*, 2010, 56, 813-828]. A kit based on this method is commercially available (Abraxis LLC, Warminster, USA), although its sensitivity does not seem sufficient and it is far from those exhibited by commercial ELISAs for other cyanotoxins. The only documented attempt to synthesize a functionalized analogue of anatoxin-a aimed at generating antibodies for this biotoxin was published in 2009, although the authors did not demonstrate having achieved the pursued objective and no further work was reported on this topic [Marc et al., *Tetrahedron Lett.*, 2009, 50, 4554-4557]. The immunoanalytical methods are based on the selective, reversible and non-covalent bond between the substance to be detected (analyte) and an antibody which recognizes it with high affinity. Depending on the analytical aim, the antibodies can be adapted to different formats such as immunoaffinity columns, lateral flow tests and immunostrips, biosensors, microarrays and primarily ELISA type tests.

To date, the preparation of antibodies capable of recognizing anatoxin-a has not been described, so no immunoanalytical methods of any kind have been developed which allow for the determination, detection, concentration or extraction of anatoxin-a using antibodies. There is therefore a need, particularly in the food, agricultural, clinical and/or environmental industry to develop analytical methods which comprise at least one antibody for anatoxin-a, preferably by means of using a kit.

DESCRIPTION OF THE INVENTION

The present invention provides bioconjugates and labeled derivatives of anatoxin-a and the use of the bioconjugates for obtaining antibodies for anatoxin-a.

Therefore a first aspect of the present invention relates to a bioconjugate of general formula (I):

[T-L-Z]$_n$—P    (I)

wherein:
T is selected from the group consisting of R-I, R-II and R-III:

R-I

R-II

R-III

L is a hydrocarbon chain of 0 to 40 carbon atoms, where the chain is linear or branched, saturated or unsaturated, and said hydrocarbon chain comprises the substitution of between 0 and 10 carbon atoms for heteroatoms which are selected from the group consisting of S, O and N; preferably L is a linear hydrocarbon chain of 0 to 20 carbon atoms and said hydrocarbon chain comprises between 0 and 4 heteroatoms selected from the group consisting of O and N, and more preferably L is a saturated linear hydrocarbon chain of 1 to 10 carbon atoms and optionally the hydrocarbon chain comprises between 1 and 4 heteroatoms selected from the group consisting of O and N; and Z is a functional group selected from:
—(C═O)NH—, —NH(C═O)—, —(C═O)S—, —S(C═O)—, —(C═O)O—, —O(C═O)—, —O(C═O)O—, —O(S═O)O—, —O(SO$_2$)O—, —NH(S═O)O—, —O(S═O)NH—, —NH(SO$_2$)O—, —O(SO$_2$)NH—, —(SO$_2$)NH—, —NH(SO$_2$)—, —O(C═O)NH—, —NH(C═O)O—, —NH(C═O)NH—, —NH(C═S)NH—, —NH—, —N(alkyl)-, —S—, —S—S—, —NH—NH—, —N═C—, —C═N—, —NH(C═NH)—, —N═N—, —O—, —CH═CH—, In a preferred embodiment, Z is selected from the group consisting of —(C═O)NH—, —NH(C═O)—, —O(C═O)NH—, —NH(C═O)O—, —NH(C═O)NH—, —NH—, —S—, More preferably Z is —(C═O)NH—.

P is a natural or synthetic peptide or polypeptide with a molecular weight greater than 2000 Daltons. The peptide or polypeptide P may or may not be bonded by means of a covalent, electrostatic interaction or another type interaction to a support. Said support may be a synthetic polymer or not, or be composed of nanomaterials such as carbon nanotubes, zeolites or mesoporous silica.

According to another preferred embodiment of the present invention, the bioconjugate of formula (I) described in this patent application is characterized in that P is selected from the group consisting of albumin, thyroglobulin, hemocyanin, beta-galactosidase, peroxidase, phosphatase and oxidase. More preferably P is peroxidase or albumin which may be egg albumin or serum albumin; and n is a number with a value of between 1 and 500; preferably n is a value of between 1 and 100.

The value of n indicates the degree of conjugation, that is to say, the molar ratio between the fraction derived from the compound of formula T-L-Z and P in the resulting bioconjugate of formula (I).

According to another preferred embodiment of the present invention, the bioconjugate of formula (I) is a bioconjugate of formula (Ia)

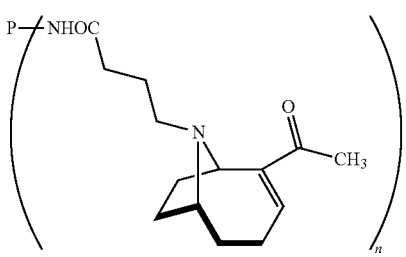

(Ia)

wherein:

P and n have been previously defined. Preferably P is albumin or peroxidase and n is a value selected between 1 and 50.

According to another preferred embodiment, the bioconjugate of formula (I) is a bioconjugate of formula (Ib)

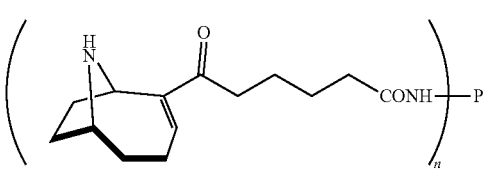

(Ib)

wherein:

P and n have been previously defined. Preferably P is albumin or peroxidase and n is a value selected between 1 and 50.

According to another preferred embodiment, the bioconjugate of formula (I) is a bioconjugate of formula (Ic)

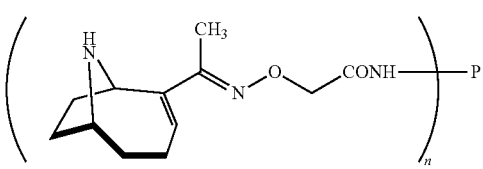

(Ic)

wherein:

P and n have been previously defined. Preferably P is albumin or peroxidase and n is a value selected between 1 and 50.

The bioconjugate of formula (I) of the present invention may be obtained by a method which comprises making react a functionalized derivative (hapten) of anatoxin-a with P, a natural or synthetic polypeptide with a molecular weight greater than 2000 Daltons by means of methods widely known in the art.

In another embodiment of the present invention, when the carrier material is a detectable nonisotopic label, the derivative is a compound of formula (II):

$[T\text{-}L\text{-}Z]_m\text{-}Q$ (II)

wherein T, L and Z have the same meaning previously defined for the bioconjugate of formula (I);

Q is a detectable nonisotopic label; and m is a number with a value between 1 and 1000, preferably m is a value selected between 1 and 100.

In the present invention, “label” is understood as any molecule or fragment which produces a signal measurable by any type of analytical technique. In the present invention, Q identifies a fragment or a nonisotopic chemical detector, label or tracer molecule.

In a preferred embodiment, Q is an enzyme, biotin, a luminescent compound, a fluorophore, a label coupled to an indirect detection system, micro or nanoparticles or others. Preferably, Q is selected from the group consisting of peroxidase, alkaline phosphatase, biotin, fluorescein or any one of the derivatives thereof, a cyanine fluorophore, a rhodamine fluorophore, a cumarin fluorophore, a ruthenium bipyridyl, luciferin or any one of the derivatives thereof, an acridinium ester, quantum dots and colloidal gold, carbon or latex micro or nanoparticles.

This compound of formula (II) may be used with an anatoxin-a antibody for determining or detecting this cyanotoxin in a sample by means of immunoassay technology.

According to a preferred embodiment, the derivative of formula (II) is a derivative of formula (IIa)

(IIa)

wherein Q is selected from the group consisting of peroxidase, biotin, fluorescein or nanoparticles, and m is a value selected between 1 and 10.

According to another embodiment that is also more preferred, the derivative of formula (II) is a derivative of formula (IIb)

(IIb)

wherein Q is selected from the group consisting of peroxidase, biotin, fluorescein or nanoparticles and m is a value selected between 1 and 10.

According to another embodiment that is also more preferred, the derivative of formula (II) is a derivative of formula (IIc)

(IIc)

wherein Q is selected from the group consisting of peroxidase, biotin, fluorescein or nanoparticles and m is a value selected between 1 and 10.

The labeled derivative of formula (II) of the present invention may be obtained by a method which comprises making react a functionalized derivative (hapten) of anatoxin-a with Q, a nonisotopic label, by means of methods widely known in the art.

The bioconjugate of formula (I) of the present invention may be used for producing antibodies, or together with an anatoxin-a antibody, for determining or detecting this cyanotoxin in a sample by means of immunoassay technology. Moreover, the labeled derivatives of formula (II) may be used together with an anatoxin-a antibody for determining or detecting this cyanotoxin in a sample by means of immunoassay technology.

In order to obtain antibodies against anatoxin-a, functionalized derivatives of said cyanotoxin (haptens) have been prepared, that is to say, structural analogues of anatoxin-a which incorporate a functional group capable of being used for the conjugation to a carrier P or label Q. This functional group is separated from the skeleton of the molecule of anatoxin-a by a spacer L. The incorporation position of the functional group to the anatoxin-a structure for the conjugation is not an obvious aspect and may be crucial for the viability of the bioconjugates of formula (I) for triggering the production of antibodies with suitable affinity and selectivity against anatoxin-a and even for the viability of the bioconjugates of formula (I) or labeled derivatives of formula (II) for acting as competitor molecules which allow for the development of a sensitive and specific immunoassay for said cyanotoxin.

In the context of this invention, the term "antibody" relates to the immunoglobin that an animal or a hybrid cell (like a hybridoma) synthesizes specifically against the immunogen of the invention (bioconjugate of the invention).

Therefore, a third aspect of the present invention relates to an antibody (from now on, antibody of the invention) generated in response to a bioconjugate of the invention, in particular to the bioconjugate of formula (I). More preferably, the antibodies are generated in response to the bioconjugate of formula (Ia), (Ib) or (Ic), more preferably to the bioconjugate of formula (Ib).

The method for obtaining the antibodies of the invention from bioconjugates of the invention may be carried out by means of immunization methods widely known in the art. The antibodies generated from a bioconjugate of the present invention may be polyclonal antibodies, monoclonal antibodies, recombinant antibodies or antibody fragments. The antibodies of the invention have high affinity and specificity towards anatoxin-a.

Another aspect of the present invention relates to an antiserum (from now on, antiserum of the invention) which comprises the antibodies of the invention.

The term, "antiserum" relates to a serum obtained following the immunization of an animal with an immunogen. The antiserum comprises specific antibodies of said immunogen generated following the immune response produced in the animal. In the context of the present invention, the immunogen is the bioconjugate of the invention and the antiserum comprises specific antibodies generated against the bioconjugate of the invention, the antibodies of the invention.

A fourth aspect of the present invention relates to a method for in vitro analysis of anatoxin-a in a sample which comprises the following steps:
a) placing the sample in contact with the antibody or the antiserum of the invention;
b) incubating the sample and the antibody (or the antiserum) of step (a) for a suitable period of time in order to produce an immunochemical reaction; and
c) determining the existence of the immunochemical reaction following the incubation of step (b).

The method of the present invention allows for the quantitative determination or qualitative analysis of the content of the anatoxin-a cyanotoxin in a sample. At the same time, the method of the present invention allows the content of anatoxin-a in different types of samples to be analyzed, for example foodstuff samples, environmental samples such as ground or surface water and isolated biological samples such as urine. Preferably, the present invention provides a method for in vitro analysis of anatoxin-a in water.

According to a preferred embodiment, the determination of the immunochemical reaction in step (c) is carried out by means of a competitive immunoassay, using a bioconjugate of formula (I) or a labeled derivative of formula (II) as the competitor. Preferably the competitive immunoassay is an ELISA type immunoassay.

The term, "immunoassay" makes reference to an analytical assay in which an immunochemical reaction for detecting or quantifying an analyte takes place. Competitive immunoassays are assays in which the analyte competes with another molecule for the bonding to the antibody.

The term, "antigen" in this patent application relates to a molecule capable of interacting specifically with an antibody. The immunochemical interaction or reaction consists of the specific and non-covalent binding between an antibody and an antigen, this may be the analyte or an antigen assay.

In the present specification, the term "assay antigen", "enzymatic antigen" or "tracer" relates to a bioconjugate of formula (I) or to a labeled derivative of formula (II) which is used in the competitive assay.

A fifth aspect of the present invention also relates to a kit for detecting anatoxin-a which uses at least one antibody of the invention. Additionally, the kit for detecting anatoxin-a may comprise a bioconjugate of formula (I) or a labeled derivative of formula (II) as are described in the present patent application.

A sixth aspect of the present invention also relates to a method for purifying and/or concentrating anatoxin-a from a sample consisting of immobilizing at least one antibody of the invention via any support and causing a sample to pass through said support so that the anatoxin-a present in said sample is retained. The subsequent elution of the anatoxin-a retained in the support by means of methods widely known in the art (change of pH, modification of the ionic strength, use of chaotropic agents) allows for the purification and/or concentration thereof in a system known as immunoaffinity chromatography.

The terms, "immunogen" and "immunogenic", as they are used in the present invention, relate to a substance which is recognized as foreign to the living organism and therefore is capable of producing or generating an immune response in a host. In the present invention, the immunogen is a bioconjugate of formula (I).

Throughout the description and the claims, the word "comprises" and the variants thereof do not intend to exclude other technical characteristics, additions, components or steps. Other objects, advantages and characteristics of the invention will emerge for the person skilled in the art in part from the description and in part from the practice of the invention.

Below, some examples and figures illustrate the form in which the preparation of various functionalized derivatives of anatoxin-a (haptens) and the corresponding bioconjugates of formula (I) may be carried out which do not intend to limit the present invention and which serve to show not only the form in which the preparation of the same may be carried out, but also the importance that the structure of the bioconjugate of formula (I) may have in order to produce antibodies with suitable affinity towards the analyte, appropriate for developing an effective immunoanalytic method.

BRIEF DESCRIPTION OF THE FIGURES

FIG. 6 standard curve for anatoxin-a with the monoclonal antibodies obtained in the indirect competitive ELISA format.

FIG. 7 standard curve for anatoxin-a with the monoclonal antibodies obtained in the direct competitive ELISA format.

FIG. 8 Enantiospecificity of the monoclonal antibodies against anatoxin-a.

EXAMPLES

The invention is illustrated below by means of tests carried out by the inventors which reveals the efficacy of the bioconjugates of formula (I) for obtaining antibodies against anatoxin-a and developing an immunoassay with high sensitivity for the same. The numbers in bold make reference to the corresponding structure which is shown in the diagrams. These examples are presented as a demonstration, but in no way may they be assumed as limiting the invention.

1. Preparation of Bioconjugates of Formula (I)

Example 1

Preparation of bioconjugates of formula (I) for T=R-I, L=$CH_2CH_2CH_2$, Z=—(C═O)NH— and P=BSA (bovine serum albumin), OVA (ovalbumin) and HRP (horseradish peroxidase).

1.1. Preparation of the Ester of N-Hydroxysuccinimide of the ANA-1 Hapten (NHS-ANA-1)

The starting material (1) was prepared from 1,2-epoxy-5-cyclooctene by adapting a previously published route [D. B. Kanne et al., *J. Am. Chem. Soc.* 1986, 108, 7864-7865].

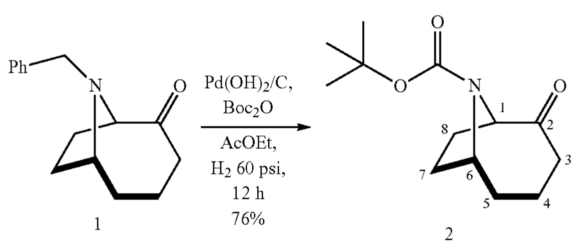

1 2

Preparation of tert-butyl 2-oxo-9-azabicyclo[4.2.1]nonane-9-carboxylate (2)

A mixture of 300 mg (1.308 mmol) of bencylamine 1, 57 mg of 20% $Pd(OH)_2$ on carbon (50% moisture) and 1.12 equivalents (320 mg, 1.465 mmol) of di-tert-butyl carbonate in 3.2 mL of AcOEt was maintained with stirring under a pressure of 60 psi of $H_2$ at room temperature for 12 hours. After this time, the mixture was filtered over celite and washed with AcOEt. The filtrate was washed with 20 mL of a $NaHCO_3$ saturated solution and brine and dried over $MgSO_4$ anhydrous. The resulting residue of the evaporation of the solvent was purified by means of silica gel chromatography, using AcOEt-hexane 9:1 as the eluent in order to obtain the protected N-Boc amine 2 as a colorless oil which solidifies at −20° C. (238 mg, 76%).

IR $v_{max}$/cm$^{-1}$ 2967, 2931, 1709, 1687, 1392, 1343, 1168, 1102. $^1$H NMR (300 MHz, $CDCl_3$) (2 rotamers in a proportion of 2:1; the data of the majority are described) δ 4.58-4.18 (2H, m, H-1 and H-6), 2.59-2.47 (1H, m, H-3), 2.40-2.25 (2H, m, H'-3 and H-7), 2.25-2.06 (2H, m, H-5 and H-8), 1.96-1.86 (1H, m, H'-7), 1.81-1.62 (4H, m, H-4, H'-5, H'-8), 1.42 (9H, s, $CMe_3$), $^{13}$C NMR (75 MHz, $CDCl_3$) δ 215.4 (C-2, C═O), 153.1 (C═O Boc) 80.4 ($CMe_3$), 65.1 (C-6), 56.6 (C-1), 41.8 (C-3), 33.0 (C-5), 30.0 (C-7), 28.5 ($CMe_3$), 26.9 (C-8), 19.4 (C-4); EMAR (ES) m/z calculated for $C_{13}H_{22}NO_3$ $[M+H]^+$ 240.1594, found 240.1587.

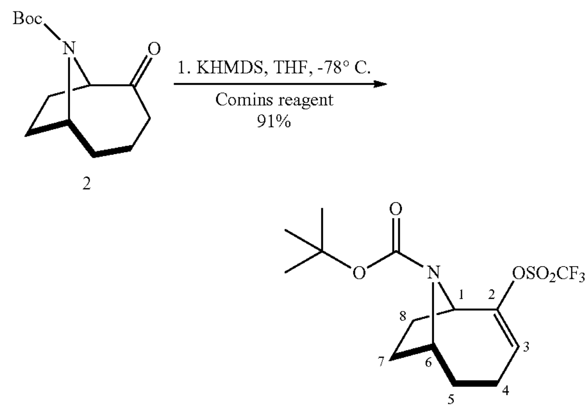

2

3

Preparation of tert-butyl 2-(((trifluoromethyl)sulfonyl)oxy)-9-azabicyclo[4.2.1]non-2-ene-9-carboxylate (3)

In a flask, a solution was prepared with 123 mg (0.514 mmol) of the ketone 2 in 6.65 mL of THF anhydrous under inert atmosphere. The solution was cooled at −78° C. and 2.0 equivalents (2.05 mL, 1.027 mL) of 0.5 M bis(trimethylsilyl)potassium amide (KHMDS) in toluene were added dropwise; the reaction was left to progress for 1.5 hours and subsequently 2.5 equivalents (504 mg, 1.284 mmol) of a solution of N-(5-chloro-2-pyridinyl)bis(trifluoromethanesulfonamide) (Comins reagent) dissolved in 0.4 mL of THF anhydrous were added. This mixture was stirred for 1 additional hour, maintaining the reaction temperature at −78° C. Finally, 2 mL of an ammonium chloride saturated solution was added at 0° C., the reaction mixture was diluted with water and extracted with AcOEt (3×15 mL). The collected organic phases were washed with brine and were dried over $MgSO_4$ anhydrous. The residue obtained after removing the solvent was purified by means of column chromatography, using hexane-AcOEt 9:1 as the eluent in order to obtain the enol triflate 3 as a colorless oil (174.0 mg, 91%). IR $v_{max}$/cm$^{-1}$ 2972, 1679, 1455, 1400, 1366, 1243, 1201, 1168, 1138, 1072, 884. $^1$H NMR (300 MHz, $CDCl_3$) (2 rotamers in a proportion of 3:1; the data of the majority are described) δ 5.79-5.72 (1H, m, H-3), 4.55 (1H, m, H-1), 4.44-4.23 (1H, m, H-6), 2.21 (2H, m, H-4), 2.20-1.64 (2H, m, H-5), 2.06 (2H, m, H-8), 2.04-1.67 (2H, m, H-7), 1.44 (9H, s, CMe₃) ¹³C NMR (75 MHz, CDCl₃) δ 154.6 (C-2), 153.1 (C=O Boc), 120.5 (C-3), 116.5 (CF₃), 80.5 (CMe₃), 58.9 (C-1), 54.9 (C-6), 32.4 (C-7), 31.0 (C-8), 30.5 (C-5), 28.3 (CMe₃), 19.7 (C-4) ¹⁹F-NMR (282 MHz, CDCl₃) δ −74.4 (s), EMAR (ES) m/z calculated for C₁₄H₂₁F₃NO₅S [M+H]⁺ 372.1009, found 372.1014.

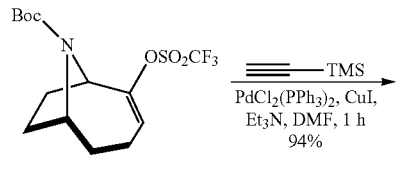

Figure 1:
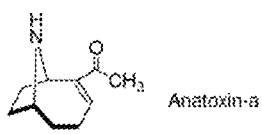
FIG. 1 structure of anatoxin-a.
Figure 2:
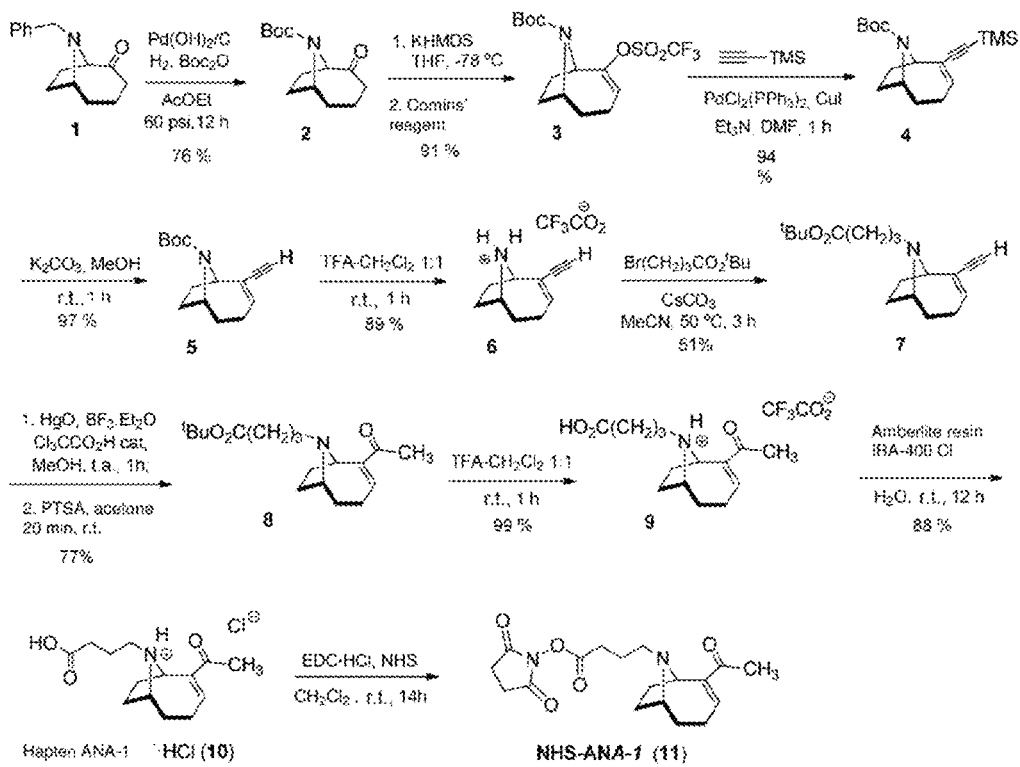
FIG. 2 diagram of the synthesis of the NHS-ANA-1 hapten.
Figure 3:
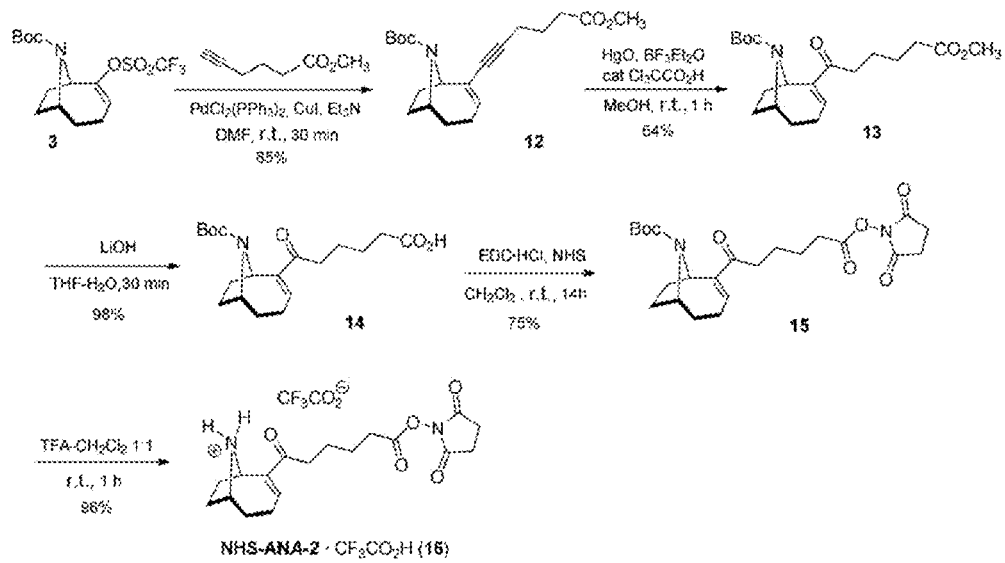
FIG. 3 diagram of the synthesis of the NHS-ANA-2 hapten.
Figure 4:
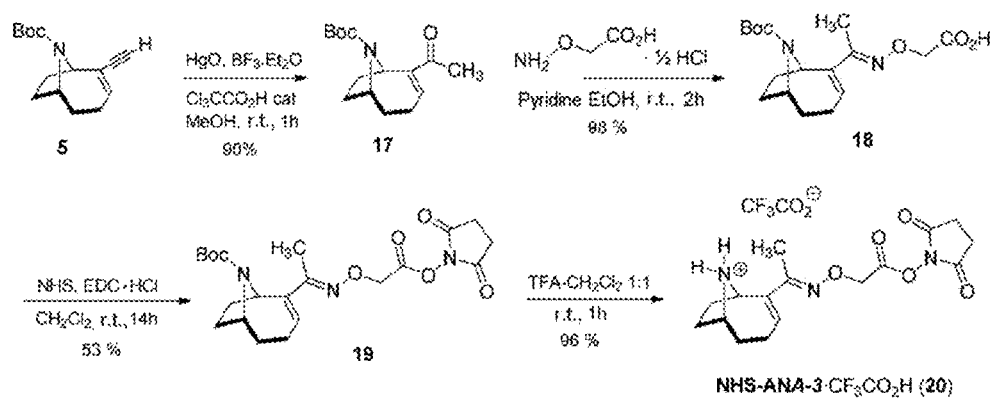
FIG. 4 diagram of the synthesis of the NHS-ANA-3 hapten.
Figure 5:
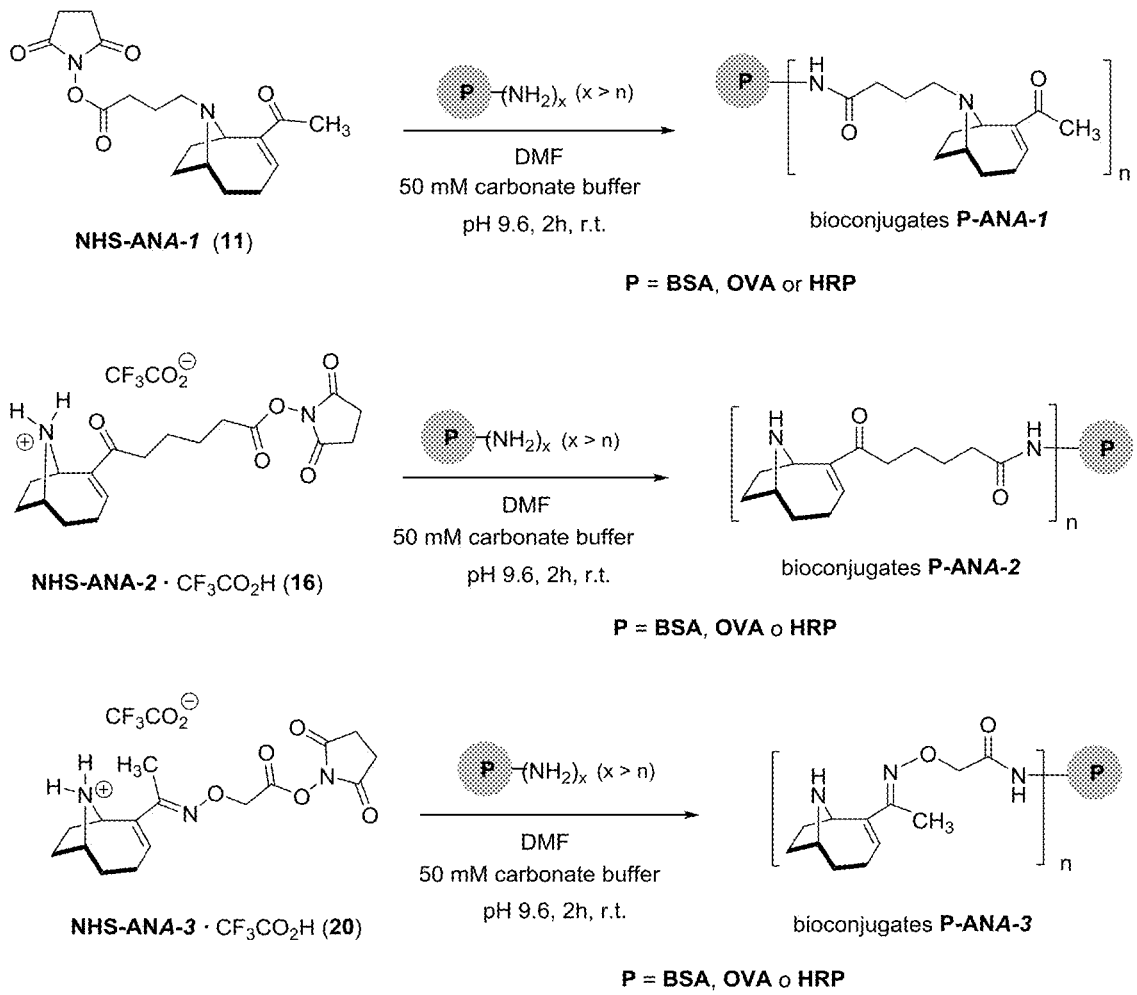
FIG. 5 diagram of the preparation of a bioconjugate of formula (I) from the corresponding functionalized derivative (hapten) of anatoxin-a.

Preparation of tert-butyl 2-((trimethylsilyl)-9-azabi-cyclo[4.2.1]non-2-ene-9 carboxylate (4)

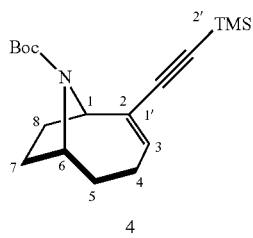

4.0 equivalents (655 μl, 4.64 mmol) of trimethylsilylacetylene were added to a mixture prepared from 430 mL (1.16 mmol) of the enol triflate 3, 81.4 mg (0.116 mmol, 10% mol) of PdCl₂(PPh₃)₂ and 11.0 mg (0.06 mmol, 5% mol) of CuI under inert atmosphere in 6.2 mL of DMF anhydrous. The resulting solution was degasified by sonication under a nitrogen current, 484 μL (3.48 mmol, 3 equivalents) of Et₃N were added and the mixture was stirred for 1 hour at room temperature. After checking the completion of the reaction by CCF (hexane: AcOEt, 8:2), the reaction mixture was diluted with 10 mL of water and was extracted with Et₂O (3×15 mL), the collected organic phases were washed with a solution of 1.5% LiCl, brine and were dried over MgSO₄ anhydrous. The residue obtained after the evaporation of the solvent was purified by means of silica column chromatography, using hexane-AcOEt 8:2 as the eluent in order to obtain the conjugated enone 4 as a colorless oil (348 mg, 94%). ¹H NMR (300 MHz, CDCl₃) (2 rotamers in a proportion of 4:1; the data of the majority are described) δ 6.12 (1H, m, H-3), 4.58 (1H, m, H-1), 4.42-4.10 (1H, m, H-6), 2.26-2.14 (2H, m, H-4), 2.20-1.89 (2H, m, H-7), 2.15-1.63 (2H, m, H-8), 2.12-1.70 (2H, m, H-5), 1.47 (9H, s, CMe₃), 0.16 (9H, s, SiMe₃); ¹³C NMR (75 MHz, CD₃Cl) δ153.4 (C=O), 138.0 (C-3), 131.7 (C-2), 106.6 (C-1'), 92.6 (C-2'), 79.6 (CMe₃), 59.8 (C-1), 55.6 (C-6), 31.4 (C-7), 31.3 (C-8), 28.8 (C-5), 28.6 (CMe₃), 24.3 (C-4), 0.15 (SiMe₃), EMAR (ES) m/z calculated for C₁₈H₃₀NO₂Si [M+H]⁺ 320.2040, found 320.2042.

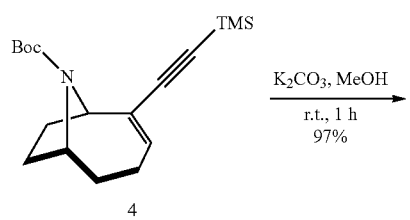

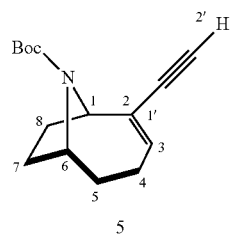

Preparation of tert-butyl 2-ethynyl-9-azabicyclo [4.2.1]non-2-ene-9-carboxylate (5)

A mixture formed from 254 mg (0.795 mmol) of the trimethylsilylated enone 4 and 5.0 equivalents (550 mg, 3.978 mmol) of K₂CO₃ anhydrous in 10 mL of MeOH was stirred at room temperature under an N₂ atmosphere, controlling its progression by CCF (hexane-AcOEt, 8:2 as the eluent). After 1 hour, the reaction mixture was diluted with 30 mL of water and extracted with CH₂Cl₂ (3×25 mL), the organic phases were washed with brine and were dried over MgSO₄ anhydrous. After evaporating the solvent, the conjugated enone 5 was obtained as a clear yellow oil, almost pure as indicated by ¹H NMR, so further purification was not required (190 mg, 97%). IR ν_max/cm⁻¹ 2973, 2928, 1685, 1404, 1362, 1248, 1168, 1106, 1007, 934, 852; ¹H NMR (300 MHz, CDCl₃) (mixture of 2 rotamers in a proportion of 2:1; the data of the majority are described) δ 6.16 (1H, dd, J=6.1, 6.1 Hz, H-3), 4.59 (1H, m, H-1), 4.40-4.18 (1H, m, H-6), 2.89 (1H, s, H-2'), 2.25 (2H, m, H-4), 2.20-2.12 (3H, m, H-5, H-7, H-8), 1.92-1.81 (1H, m, H'-7), 1.71-1.60 (2H, m, H'-5, H'-8), 1.46 (9H, s, CMe₃); ¹³C NMR (75 MHz, CD₃Cl) δ 155.6 (C=O), 138.3 (C-3), 130.1 (C-2), 85.0 (C-1'), 79.7 (CMe₃), 76.0 (C-2'), 60.0 (C-1), 55.6 (C-6), 31.8 (C-8), 31.2 (C-7), 29.2 (C-5), 28.6 (CMe₃), 24.2 (C-4); EMAR (ES) m/z calculated for C₁₅H₂₂NO₂ [M+H]⁺ 248.1645, found 248.1645.

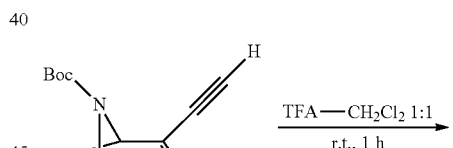

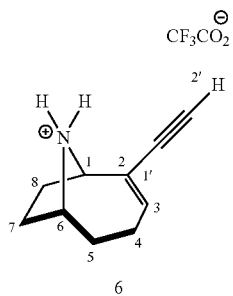

Preparation of trifluoroacetate 2 ethynyl-9-azabicy-clo[4.2.1]non-2-ene-9-io (6)

A solution was prepared from 0.5 mL of recently distilled trifluoroacetic acid in 0.5 mL of dry CH₂Cl₂, which was added under inert atmosphere to 31.0 mg (0.125 mmol) of enone 5. The mixture was stirred at room temperature for 1 hour and subsequently the solvent and excess acid were removed under reduced pressure in order to obtain a brownish oily residue corresponding to the salt with the trifluoroacetic acid of the conjugated aza-bicyclo-enone 6 (23.5 mg, 89%) which was brought directly to the following reaction step without further purification. $^1$H NMR (300 MHz, CDCl$_3$) δ 6.43 (1H, m, H-3), 4.38 (2H, m, H-1), 4.28 (1H, m, H-6), 3.0 (1H, s, H-2'), 2.45-1.77 (8H, m, H-5, H-8, H-7, H-4). $^{19}$F NMR (282 MHz, CDCl$_3$) δ −76.4.

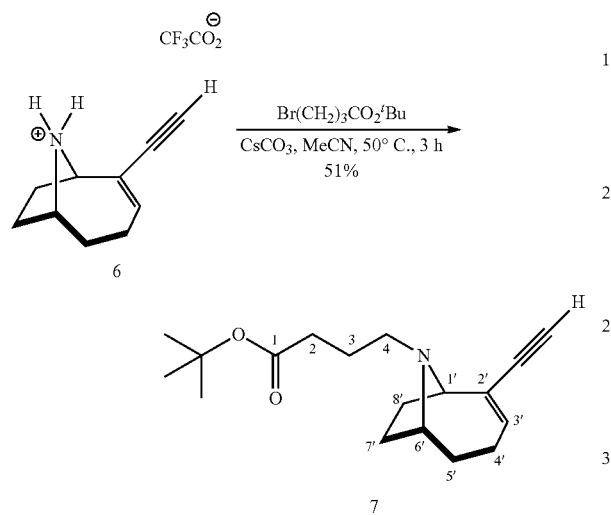

Preparation of tert butyl 4-(2-ethynyl-9-azabicyclo[4.2.1]non-2-ene-9-yl) butanoate (7)

A solution was prepared from 81.0 mg (0.419 mmol) of the alkaline salt 6, 3.0 equivalents (1.26 mmol) of CsCO$_3$ and 2.5 equivalents (1.04 mmol) of tert-butyl 4-bromobutanoate in 1.5 mL of anhydrous acetonitrile under an N$_2$ atmosphere. The resulting reaction mixture was stirred at 50° C. for 3 hours and at the end of the reaction it was diluted with water and a saturated solution of NaHCO$_3$, extracted with CH$_2$Cl$_2$ (3×20 mL) and the collected organic phases were washed with brine and were dried over MgSO$_4$ anhydrous. The residue resulting after the evaporation of the solvent was purified by silica gel column chromatography using CHCl$_3$-MeOH 9:1 as the eluent in order to obtain N-alkylated alkyne 7 as a slightly yellow color oil (61.0 mg, 51%). IR v$_{max}$/cm$^{-1}$ 3294.9, 2973.0, 2927.7, 1725.8, 1421.5, 1365.8, 1254.9, 1149.4, 951.4, 845.4; $^1$H NMR (300 MHz, CDCl$_3$) (mixture of 2 rotamers in a proportion of 6:1; the data of the majority are described) δ 6.25 (1H, ddd, J=8.2, 8.2, 0.6 Hz, H-3'), 3.80 (1H, m, H-1'), 3.47 (1H, m, H-6'), 2.86 (1H, s, C≡C—H), 2.60 (2H, m, H-4), 2.36 and 1.80 (2H, m, H-8' and H'-8'), 2.32-2.13 (2H, m, H-4'), 2.26 (2H, m, H-2), 2.23-2.15 (2H, m, H-5'), 2.06 and 1.64 (2H, m, H-7' and H'-7'), 1.80 (2H, m, H-3), 1.44 (9H, s, CMe$_3$); $^{13}$C NMR (75 MHz, CD$_3$Cl) δ 173.3 (C-1), 138.9 (C-3'), 129.1 (C-2'), 86.8 (C≡CH), 80.1 (CMe$_3$), 75.4 (C≡CH), 64.4 (C-1'), 60.5 (C-6'), 46.4 (C-4), 33.9 (C-2), 31.5 (C-8'), 28.3 (C-7'), 28.2 (CMe$_3$) 25.24 (C-5'), 24.54 (C-4'), 23.84 (C-3); EMAR (ES) m/z calculated for C$_{18}$H$_{28}$NO$_2$ [M+H]$^+$ 290.2115 found 290.2119.

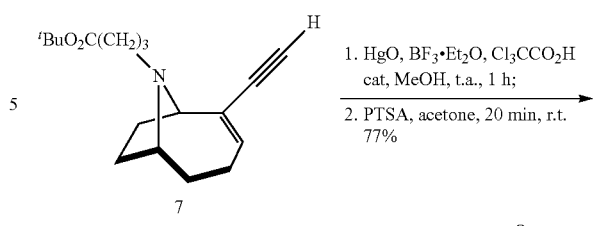

Preparation of tert-butyl 4-(2-acetyl-9-azabicyclo[4.2.1]non-2-ene-9-yl) butanoate (8). 4.6 mL of a solution prepared from 2 mg of trichloroacetic acid and 50 μL of BF$_3$.Et$_2$O in 10 mL of MeOH anhydrous were added under inert atmosphere over a solution of alkyne 7 (170.0 mg, 0.587 mmol) and 0.5 equivalents of HgO (63.7 mg, 0.293 mmol) in 2.4 mL of MeOH anhydrous. The resulting reaction mixture was stirred at room temperature, controlling the same by CCF (CHCl$_3$-MeOH, 9:1), until its conclusion. After approximately 1 hour, the reaction mixture was poured over 15 mL of cold water and 5 mL of a saturated solution of NaHCO$_3$, extracted with CH$_2$Cl$_2$ (3×15 mL) and the organic phases were washed with brine and were dried over MgSO$_4$ anhydrous. After removing the solvent, a yellow oil was obtained which was subjected directly to acidic hydrolysis using 1.5 equivalents (167.2 mg, 0.88 mmol) of p-toluenesulfonic acid (PTSA H$_2$O) in 3 mL of acetone; the reaction was stirred at room temperature for 20 minutes. Lastly, the reaction mixture was processed by dilution with 10 mL of H$_2$O and 5 mL of a saturated solution of NaHCO$_3$, extracted with CH$_2$Cl$_2$ (3×10 mL) and the collected organic phases were washed with brine and were dried over Na$_2$SO$_4$ anhydrous. The removal of the solvent at reduced pressure provides a slightly brown oily residue which was purified by column chromatography using CHCl$_3$ with 0.5% of Et$_3$N as the eluent in order to obtain the N-alkylated anatoxin-a 8 as a colorless oil (139 mg, 77%). $^1$H NMR (300 MHz, CDCl$_3$) δ 6.92 (1H, m, H-3'), 4.52 (1H, apparent d, J=10.6 Hz, H-1'), 3.49 (1H, m, H-6'), 2.48-2.35 (2H, m, H-4), 2.43-2.35 (2H, m, H-4'), 2.27 (3H, s, Me), 2.31 and 1.86 (2H, m, H-8' and H'-8'), 2.10 and 1.63 (2H, m, H-7' and H'-7'), 2.23-2.17 (2H, m, H-2), 1.85-1.72 (2H, m, H-5') 1.73-1.63 (2H, m, H-3), 1.41 (9H, s, CMe$_3$); $^{13}$C NMR (75 MHz, CDCl$_3$) δ 199.2 (COMe), 173.2 (CO$_2$), 148.6 (C-2'), 143.2 (C-3'), 80.0 (CMe$_3$), 60.6 (C-6'), 56.7 (C-1'), 48.1 (C-4), 33.7 (C-2), 31.3 (C-8'), 28.6 (C-7'), 28.2 (CMe$_3$), 25.6 (MeCO), 25.5 (C-5'), 25.0 (C-4'), 24.2 (C-3); EMAR (ES) m/z calculated for C$_{18}$H$_{30}$NO$_3$ [M+H]$^+$ 308.2220 found 308.2234.

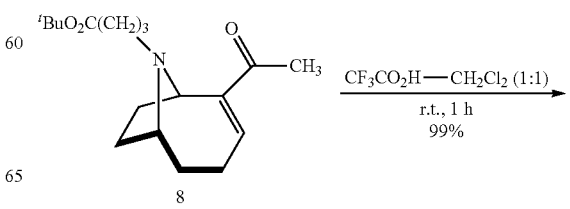

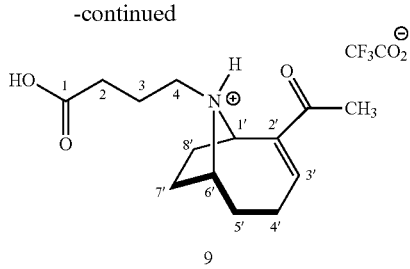

Preparation of 2,2,2-trifluoroacetate of 4-2(2-acetyl-9-(3-carboxypropyl)-azabicyclo[4.2.1]non-2-ene-9-io (hapten ANA-1, 9)

30.5 mg (99.0 µmol) of the tert-butylic ester 8 were treated with 1 mL of a 1:1 mixture of $CF_3CO_2H:CH_2Cl_2$. The resulting solution was stirred at room temperature for 1 hour. When the reaction concluded, the solvent was evaporated at reduced pressured until dryness, obtaining the hapten ANA-1 (9) in the form of the salt of trifluoroacetic acid as a colorless oil (36 mg, 99%). IR $v_{max}/cm^{-1}$ 2915.9, 2848.3, 1669.1, 1418.4, 1198.0, 1132.8, 754; $^1$H NMR (300 MHz, $CD_3OD$) δ 7.50 (1H, m, H-3'), 5.19 (1H, apparent t, J=11.5 Hz, H-1'), 4.22 (1H, m, H-6'), 3.16 (2H, m, H-4), 2.65-2.55 (2H, m, H-4'), 2.47 (2H, m, H-2), 2.35 (3H, s, Me), 2.23 and 2.03 (2H, m, H-8' and H'-8'), 2.19 and 1.85 (2H, m, H-7' and H'-7'), 2.03 (2H, m, H-3), 1.89-1.79 (2H, m, H-5); $^{13}$C NMR (75 MHz, $CDCl_3$) δ 196.0 (COMe), 176.0 ($CO_2$), 161.4 ($F_3C\ CO_2$-), 149.0 (C-2'), 148.0 (C-3'), 64.3 (C-6'), 57.0 (C-1'), 49.0 (C-4), 32.9 (C-2), 32.9 (C-8'), 29.3 (C-7'), 26.8 (C-5'), 25.4 (Me), 23.5 (C-4'), 20.7 (C-3); $^{19}$F NMR (282 MHz, $CD_3OD$) δ -77.73; EMAR (ES) m/z calculated for $C_{14}H_{22}NO_3$ $[M+H]^+$ 252.1594, found 252.1596.

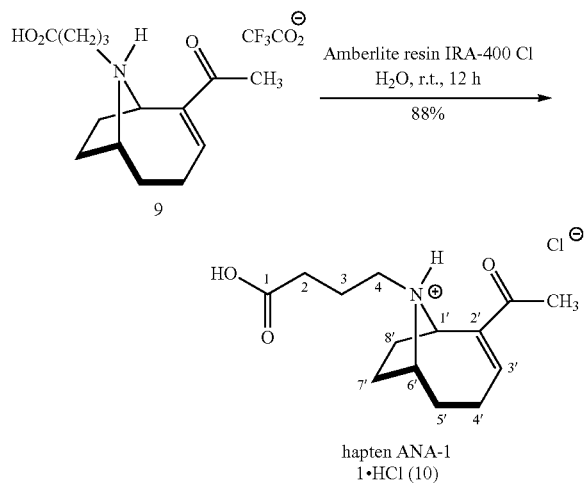

Preparation of the hydrochloride of 4-(2-acetyl-9-azabicyclo[4.2.1]non-2-ene-9-yl) butanoic acid (hydrochloride of Hapten ANA-1, 10)

80 mg of amberlite resin IRA-400, previously conditioned, was added to a solution prepared from 36 mg (0.098 mmol) of the salt of the trifluoroacetic acid of the Hapten ANA-1 (9) in 1 mL of Milli-Q $H_2O$ and the suspension was left under gentle stirring overnight. The reaction mixture was filtered to separate the resin, and the aqueous filtrate was lyophilized in order to obtain a very hygroscopic foamy solid corresponding to the hydrochloride of the Hapten ANA-1 (10) (24.9 mg, 88%). $^1$H NMR (300 MHz, $CDCl_3$) δ 7.33 (1H, apparent t, J=5.9 Hz, H-3'), 5.13 (1H, apparent d, J=7.9 Hz, H-1'), 4.14 (1H, m, H-6'), 3.01 (2H, m, H-4), 2.59 (2H, m, H-4'), 2.42 (2H, m, H-2), 2.42 and 1.96 (2H, m, H-8' and H'-8'), 2.35 (3H, s, Me), 2.32 and 1.96 (2H, m, H-7' and H'-7'), 1.96 (2H, m, H-3), 1.81-1.72 (2H, m, H-5'); $^{13}$C NMR (75 MHz, $CDCl_3$) δ 196.0 (COMe), 176.0 ($CO_2$), 149.0 (C-2'), 148.0 (C-3'), 64.3 (C-6'), 57.0 (C-1'), 49.0 (C-4), 33.0 (C-2), 32.9 (C-8'), 29.3 (C-7'), 26.8 (C-5'), 25.4 (Me), 23.5 (C-4'), 20.7 (C-3); EMAR (ES) m/z calculated for $C_{14}H_{22}NO_3$ $[M+H]^+$ 252.1594, found 252.1597.

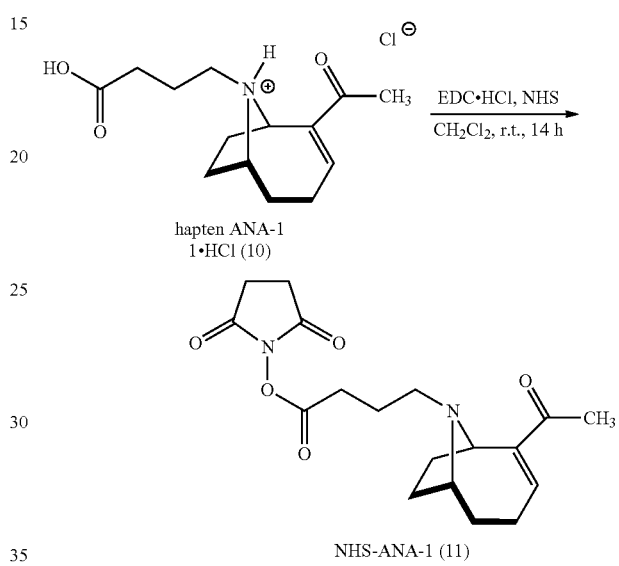

Preparation of the N-hydroxysuccinimidyl ester of the hapten ANA-1 (11)

A solution was prepared from 13.2 mg (0.046 mmol) of the hydrochloride of the hapten ANA-1 (10), 1.5 equivalents (7.9 mg, 0.069 mmol) of N-hydroxysuccinimide and 1.5 equivalents (13.2 mg, 0.069 mmol) of EDC HCl in 900 mL of dry $CH_2Cl_2$ under $N_2$ atmosphere. The reaction mixture was stirred at room temperature for 17 hours. After this time, the conclusion of the reaction was confirmed by CCF using acetone-chloroform 9:1 as the eluent, and the reaction mixture was concentrated until dryness under vacuum and the obtained residue was dissolved in DMF in order to obtain a solution of approximately 50 mM of the active ester NHS-ANA-1 (11) which was used directly for preparing the corresponding bioconjugates.

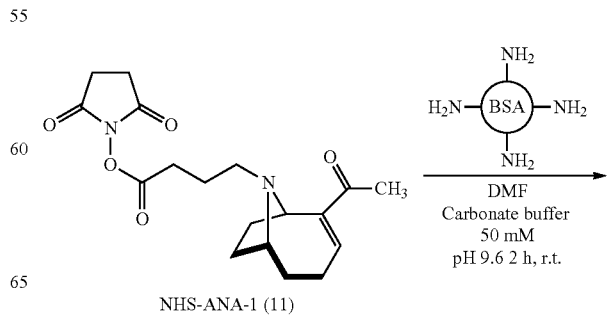

-continued

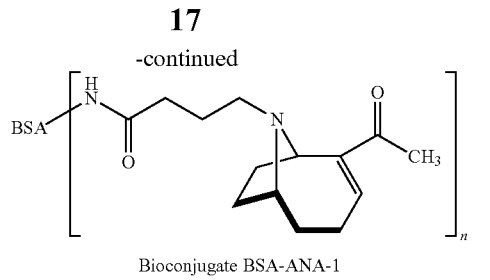

Bioconjugate BSA-ANA-1

1.2. Preparation of a bioconjugate of the hapten ANA-1 with BSA (BSA-ANA-1)

200 μL of the solution of the active ester NHS-ANA-1 (11) in DMF obtained in the previous reaction (approximately 50 mM) was slowly added and with constant stirring over 1.8 mL of a BSA solution (15 mg/mL) in 50 mM carbonate buffer, pH 9.6. The conjugation reaction was incubated for 2 hours with gentle stirring at room temperature. After this time, the conjugates were purified by molecular exclusion using 100 mm sodium phosphate, pH 7.4, as the elution buffer. After purification, the collected fractions which contained the BSA bioconjugate were brought to a final concentration of 1 mg/mL with elution buffer and were stored at −20° C.

In order to determine the haptenic charge (n) obtained in the conjugate, an aliquot of 100 μL of the purified bioconjugate BSA-ANA-1 was dialyzed (dialysis against 5 l of deionized water with at least 2 to 3 changes of water per 24 hours at 4° C.; lastly, the dialyzed product was lyophilized and the number of hapten molecules conjugated per BSA molecule was determined by means of MALDI-TOF-MS (n=8, see Table 1, entry 2).

TABLE 1

Values of the haptenic charge of the protein conjugates as determined by MALDI-TOF-MS

|   |         | $RM_0$ | m/z     | Δ(m/z) | Δm/hapten | n    |
|---|---------|--------|---------|--------|-----------|------|
| 1 | BSA     | —      | 66431.0 | —      | —         | —    |
| 2 | BSA-ANA-1 | 24   | 68316.2 | 1885.2 | 233.3     | 8.0  |
| 3 | BSA-ANA-2 | 24   | 69810.5 | 3379.5 | 233.3     | 14.5 |
| 4 | BSA-ANA-3 | 24   | 69952.8 | 3522.5 | 220.1     | 16.0 |
| 5 | OVA     | —      | 42749.0 | —      | —         | —    |
| 6 | OVA-ANA-1 | 8    | 43504.0 | 755.0  | 233.3     | 3.2  |
| 7 | OVA-ANA-2 | 8    | 44715.0 | 1966.0 | 233.3     | 8.4  |
| 8 | OVA-ANA-3 | 8    | 44500.0 | 1751.0 | 220.1     | 7.9  |
| 9 | HRP     | —      | 43973.5 | —      | —         | —    |
| 10 | HRP-ANA-1 | 10  | n.d.    | n.d.   | n.d.      | n.d. |
| 11 | HRP-ANA-2 | 10  | 44937.4 | 963.5  | 233.3     | 4.1  |
| 12 | HRP-ANA-3 | 10  | 44529.0 | 555.5  | 220.1     | 2.5  |

$RM_0$: initial hapten/protein molar ratio used for the conjugation
n: hapten/protein molar ratio obtained for each conjugate
Δ(m/z): (m/z conjugate) − (m/z reference protein)
Δm/hapten: mass increase for each conjugated hapten molecule
n.d.: not determined

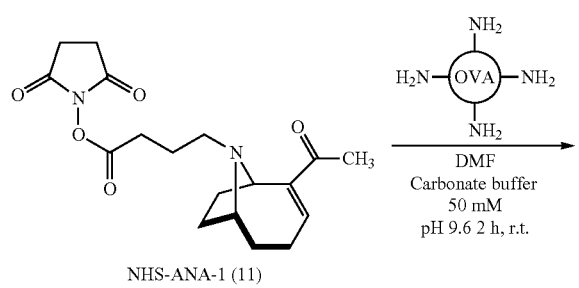

NHS-ANA-1 (11)

-continued

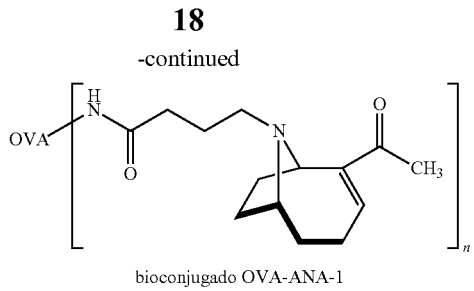

bioconjugado OVA-ANA-1

1.3 Preparation of a bioconjugate of the hapten ANA-1 with OVA (OVA-ANA-1)

From a solution of 50 mm in DMF of the activated hapten NHS-ANA-1 (11), 100 μL was taken and slowly added with constant stirring to a 1.9 mL OVA solution (15 mg/mL) in 50 mM carbonate buffer, pH 9.6. After 2 hours of reaction under gentle stirring at room temperature, the bioconjugate was purified as previously described for the BSA conjugate. The collected fractions were brought to a final concentration of 1 mg/mL in elution buffer with 0.01% (v/v) thimerosal and stored at −20° C. An aliquot of the conjugate OVA-ANA-1 recently obtained was dialyzed and lyophilized to calculate the efficacy of the conjugation in terms of the number of hapten molecules (11) coupled to the protein by means of MALDI-TOF-MS (n=3.2, see Table 1, entry 6).

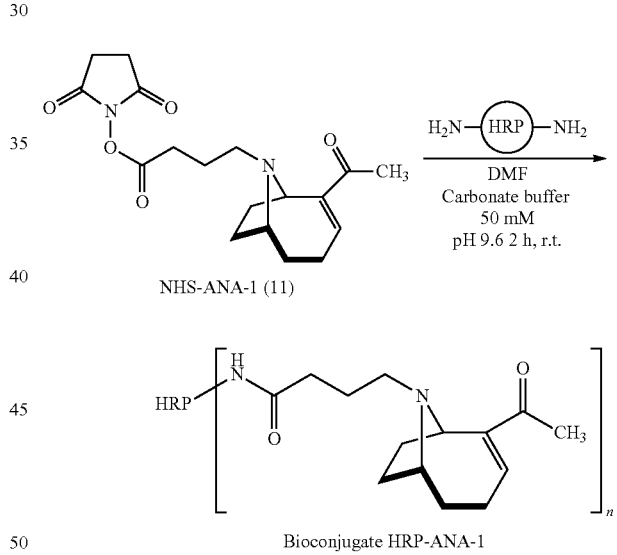

NHS-ANA-1 (11)

Bioconjugate HRP-ANA-1

1.4 Preparation of a Bioconjugate of the Hapten ANA-1 with HRP (HRP-ANA-1)

From a solution of 5 mm of the activated hapten NHS-ANA-1 (11) in DMF, 100 μL was taken and slowly added with constant and gentle stirring over 0.9 mL of a HRP solution at a concentration of 2.5 mg/mL in 50 mM carbonate buffer, pH 7.4. The conjugation reaction was incubated for 2 hours at room temperature. Subsequently the bioconjugate was purified following the method previously described for the BSA and OVA bioconjugates and was brought to known concentrations of between 250-650 μg/mL in PBS buffer with 1% BSA (w/v) and 0.02% (w/v) thimerosal and stored at 4° C.

Example 2

Preparation of Bioconjugates of Formula (I) for T=R-II, L=CH$_2$CH$_2$CH$_2$CH$_2$, Z=—(C=O)NH— and P=BSA, OVA and HRP.

2.1 Preparation of the Ester of N-Hydroxysuccinimidyl of the Hapten ANA-2 (NHS-ANA-2)

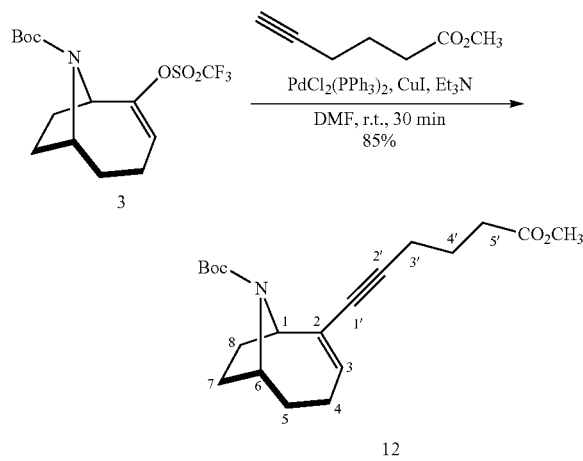

Preparation of methyl 2-(6-methoxy-6-oxohex-1-ene-1-yl)-9-azabicyclo[4.2.1]non-2-ene-9-carboxylate (12)

1.5 mL of DMF anhydrous and 4.0 equivalents (153 µl, 1.167 mmol) of commercial methyl 5-hexenoate were added to a mixture prepared from 108 mg (0.291 mmol) of the enol triflate 3, 20.4 mg (10% mol, 0.029 mmol) of PdCl$_2$(PPh$_3$)$_2$ and 2.7 mg (5% mol, 0.014 mmol) of CuI under N$_2$ atmosphere. The resulting solution was degasified by vacuum cycles under a nitrogen current and 3.0 equivalents (122 µL, 0.875 mmol) of Et$_3$N was added. After 1 hour of stirring at room temperature, it was checked by CCF that the starting triflate had been completely consumed. The reaction mixture was diluted with 10 mL of water and extracted with Et$_2$O (3×15 mL); the organic phases were successively washed with a solution of 1.5% LiCl and brine and were dried over MgSO$_4$ anhydrous. The residue obtained after the evaporation of the solvent was purified by silica gel column chromatography using hexane-AcOEt 9:1 as the eluent in order to firstly obtain the homocoupling product of the alkyne (10.9 mg, 11%), followed by the cross coupling product of the conjugated enone, 12, as a colorless oil (86.4 mg, 85%). IR $v_{max}$/cm$^{-1}$ 2953, 2400, 2350, 1733, 1690, 1402.5, 1365.1, 1164.7; $^1$H NMR (300 MHz, CDCl$_3$) (mixture of 2 rotamers in a proportion of 2:1; the data of the majority are described) δ 5.94 (1H, dd, J=11.6, 5.5 Hz, H-3), 4.51 (1H, m, H-1), 4.39-4.13 (1H, m, H-6), 3.66 (3H, s, CO$_2$Me), 2.43 (2H, t, J=7.4 Hz, H-5'), 2.31 (2H, t, J=6.9 Hz, H-3'), 2.25-2.18 (2H, m, H-4), 2.16-2.04 (3H, m, H-8, H-7), 1.83 (2H, dt, J=6.8 Hz, H-4'), 1.83-1.68 (3H, m, H-5, H'-7), 1.44 (9H, s, CMe$_3$ Boc); $^{13}$C NMR (75 MHz, CDCl$_3$) δ 173.1 (CO$_2$CH$_3$), 153.6 (C=O Boc), 135.2 (C-3), 130.9 (C-2), 87.4 (C-2'), 82.6 (C-1'), 79.4 (CMe$_3$ Boc), 60.5 (C-1), 55.1 (C-6), 51.7 (CO$_2$CH$_3$), 32.9 (C-5'), 31.3 (C-7), 30.2 (C-8), 29.4 (C-5), 28.6 (CMe$_3$ Boc), 24.1 (C-4'), 23.6 (C-4), 18.9 (C-3'), EMAR (ES) m/z calculated for C$_{20}$H$_{30}$NO$_4$ [M+H]$^+$ 348.2169, found 348.2168.

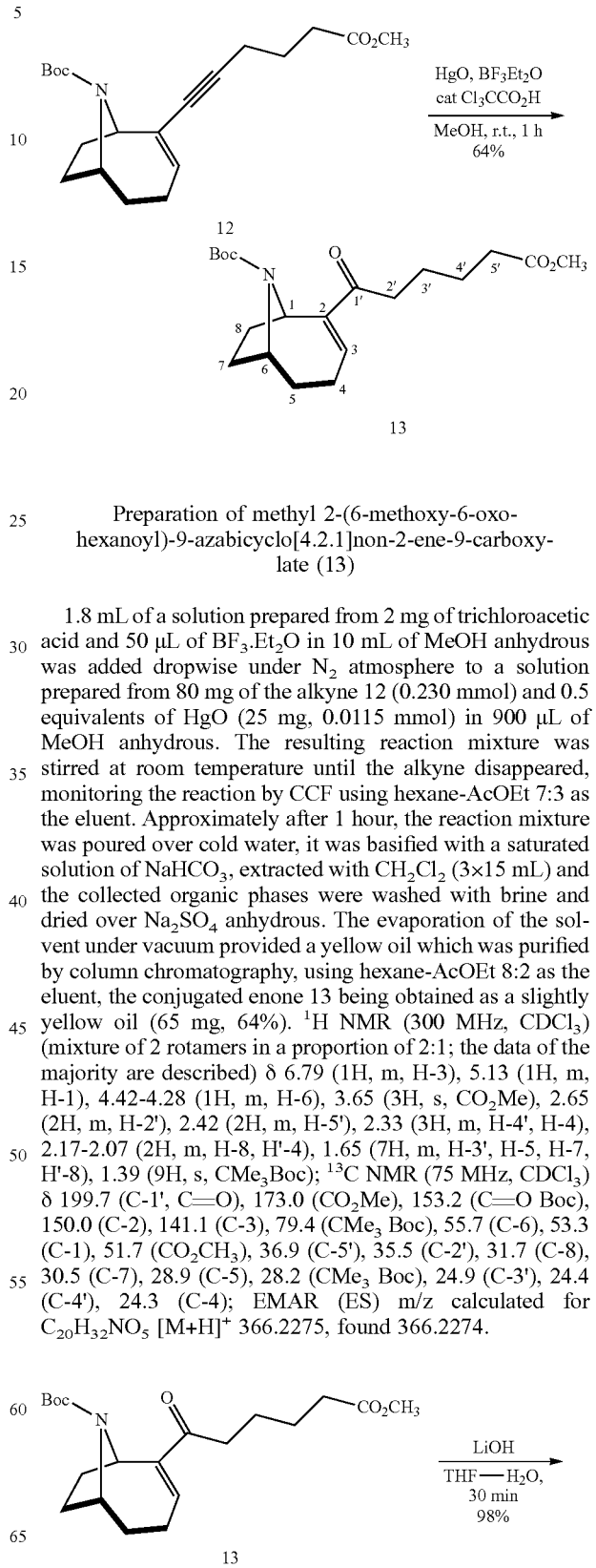

Preparation of methyl 2-(6-methoxy-6-oxo-hexanoyl)-9-azabicyclo[4.2.1]non-2-ene-9-carboxylate (13)

1.8 mL of a solution prepared from 2 mg of trichloroacetic acid and 50 µL of BF$_3$.Et$_2$O in 10 mL of MeOH anhydrous was added dropwise under N$_2$ atmosphere to a solution prepared from 80 mg of the alkyne 12 (0.230 mmol) and 0.5 equivalents of HgO (25 mg, 0.0115 mmol) in 900 µL of MeOH anhydrous. The resulting reaction mixture was stirred at room temperature until the alkyne disappeared, monitoring the reaction by CCF using hexane-AcOEt 7:3 as the eluent. Approximately after 1 hour, the reaction mixture was poured over cold water, it was basified with a saturated solution of NaHCO$_3$, extracted with CH$_2$Cl$_2$ (3×15 mL) and the collected organic phases were washed with brine and dried over Na$_2$SO$_4$ anhydrous. The evaporation of the solvent under vacuum provided a yellow oil which was purified by column chromatography, using hexane-AcOEt 8:2 as the eluent, the conjugated enone 13 being obtained as a slightly yellow oil (65 mg, 64%). $^1$H NMR (300 MHz, CDCl$_3$) (mixture of 2 rotamers in a proportion of 2:1; the data of the majority are described) δ 6.79 (1H, m, H-3), 5.13 (1H, m, H-1), 4.42-4.28 (1H, m, H-6), 3.65 (3H, s, CO$_2$Me), 2.65 (2H, m, H-2'), 2.42 (2H, m, H-5'), 2.33 (3H, m, H-4', H-4), 2.17-2.07 (2H, m, H-8, H'-4), 1.65 (7H, m, H-3', H-5, H-7, H'-8), 1.39 (9H, s, CMe$_3$Boc); $^{13}$C NMR (75 MHz, CDCl$_3$) δ 199.7 (C-1', C=O), 173.0 (CO$_2$Me), 153.2 (C=O Boc), 150.0 (C-2), 141.1 (C-3), 79.4 (CMe$_3$ Boc), 55.7 (C-6), 53.3 (C-1), 51.7 (CO$_2$CH$_3$), 36.9 (C-5'), 35.5 (C-2'), 31.7 (C-8), 30.5 (C-7), 28.9 (C-5), 28.2 (CMe$_3$ Boc), 24.9 (C-3'), 24.4 (C-4'), 24.3 (C-4); EMAR (ES) m/z calculated for C$_{20}$H$_{32}$NO$_5$ [M+H]$^+$ 366.2275, found 366.2274.

-continued

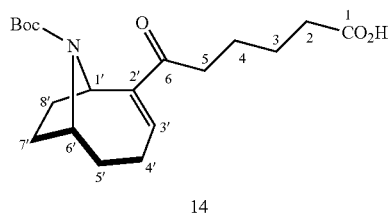

14

Preparation of 6-(9-(tert-butoxycarbonyl)-9-azabicyclo[4.2.1]non-2-ene-2-yl)-6-oxo-hexanoic acid (14)

A solution of 97 mg (0.27 mmol) of methyl ester 13 was prepared in 2 mL of THF, it was cooled in an ice bath and a cold solution of 2 mL of an aqueous solution 2.7 m (5.4 mmol, 10 final equivalents) of LiOH was added dropwise with stirring. After agitating at room temperature for 30 mins, the reaction mixture was poured over ice water and it was acidified to pH 2-3 with a 1 M cold aqueous solution of KHSO$_4$. The mixture was extracted with AcOEt (3×15 mL) and the combined organic phases were washed with brine and were dried over Na$_2$SO$_4$ anhydrous. The removal of the solvent under vacuum provided the carboxylic acid 14 as a colorless oil (93 mg, 98%) which appeared to be practically pure by means of NMR and therefore it was used in the following step without additional purification. IR $v_{max}$/cm$^{-1}$ 2973, 2931.6, 2356.8, 1662.4, 1409, 1365.1, 1246.5, 1216, 1166.9, 1115.8, 931.7, 750; $^1$H NMR (300 MHz, CDCl$_3$) (a mixture of 2 rotamers in a proportion of 2:1; the data of the majority are described), δ 6.79 (1H, m, H-3'), 5.13 (1H, apparent d, J=8.9 Hz, H-1'), 4.44-4.25 (1H, m, H-6'), 2.65 (2H, m, H-5), 2.42 (5H, m, H-2, H-4', H-8'), 2.10 (4H, m, H-3, H'-8', H-7'), 1.65 (5H, m, H-4, H-5', H'-7'), 1.39 (9H, s, CMe$_3$ Boc); $^{13}$C NMR (75 MHz, CDCl$_3$) δ 199.6 (C=O, C-6), 178.9 (CO$_2$H), 157.6 (C=O Boc), 149.9 (C-2'), 141.2 (C-3'), 79.6 (CMe$_3$ Boc), 55.1 (C-6'), 53.3 (C-1'), 36.7 (C-5), 33.6 (C-2), 31.5 (C-8'), 31.1 (C-7'), 30.5 (C-4), 28.9 (C-5'), 28.5 (CMe$_3$ Boc), 24.5 (C-4'), 24.3 (C-3); EMAR (ES) m/z calculated for C$_{19}$H$_{30}$NO$_5$ [M+H]$^+$ 352.2118, found 352.2131.

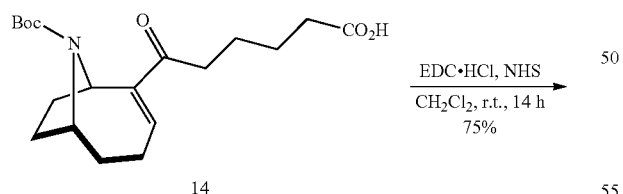

14

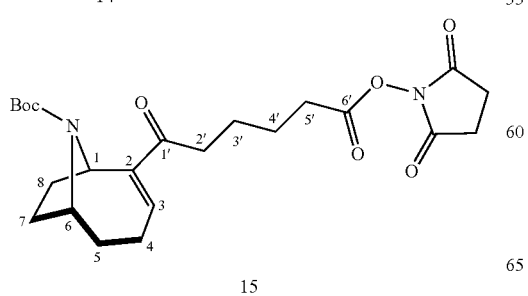

15

Preparation of tert-butyl 2-(6-((2,5-dioxopyrrolidine-1-yl)oxy)-6-oxohexanoyl)-9-azabicyclo[4.2.1]non-2-ene-9-carboxylate (15)

A solution was prepared from 80 mg (0.228 mmol) of the acid 14, 1.5 equivalents (39.3 mg, 0.341 mmol) of N-hydroxysuccinimide and 1.5 equivalents (65.4 mg, 0.341 mmol) of EDC HCl in 3 mL of dry CH$_2$Cl$_2$ under N$_2$ atmosphere. The reaction mixture was stirred at room temperature for 17 hours. After this time, the conclusion of the reaction was confirmed by CCF using acetone-chloroform 9:1 as the eluent. The reaction mixture was diluted with CH$_2$Cl$_2$, 5 mL of a saturated solution of NH$_4$Cl was added and it was extracted with the same solvent (3×10 mL). The combined organic phases were washed with brine and were dried with Na$_2$SO$_4$ anhydrous. After evaporating the solvent, a colorless oil was obtained which was purified by column chromatography using CHCl$_3$ as the eluent in order to obtain the N-hydroxysuccinimide ester 15 (77 mg, 75%). $^1$H NMR (300 MHz, CDCl$_3$) (a mixture of 2 rotamers in a proportion of 2:1; the data of the majority are described), δ 6.79 (1H, m, H-3), 5.13 (1H, m, H-1), 4.44-4.25 (1H, m, H-6), 2.83 (4H, s broad, COCH$_2$CH$_2$CO), 2.65 (2H, m, H-2'), 2.42 (5H, m, H-5', H-4, H-8), 2.10 (4H, m, H-3', H'-8, H-7), 1.65 (5H, m, H-4', H-5, H'-7), 1.39 (9H, s, CMe$_3$ Boc); $^{13}$C NMR (75 MHz, CDCl$_3$) δ 199.6 (C=O, C-1'), 168.9 (COCH$_2$CH$_2$CO), 165.5 (C=O, C-6'), 157.6 (C=O Boc), 149.9 (C-2), 141.2 (C-3), 79.6 (CMe$_3$ Boc), 55.1 (C-6), 53.3 (C-1), 36.7 (C-2'), 33.6 (C-5'), 31.5 (C-8), 31.1 (C-7), 30.5 (C-4'), 28.9 (C-5), 28.5 (CMe$_3$ Boc), 25.6 (COCH$_2$CH$_2$CO), 24.5 (C-4), 24.3 (C-3'); EMAR (ES) m/z calculated for C$_{23}$H$_{33}$N$_2$O$_7$ [M+H]$^+$ 449.2282, found 449.2281.

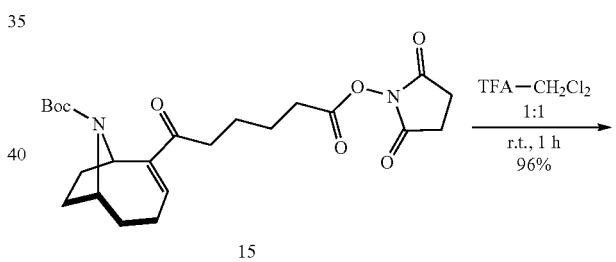

15

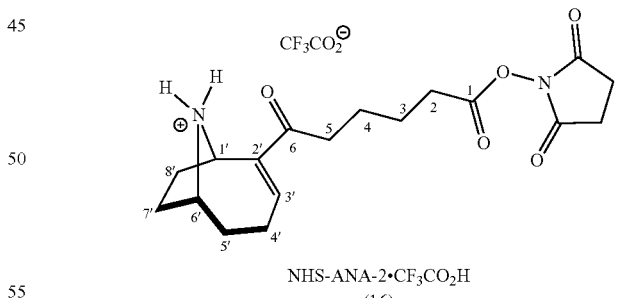

NHS-ANA-2•CF$_3$CO$_2$H
(16)

Preparation of 2,5-dioxopyrollidine-1-yl-6-(9-azabicyclo[4.2.1]non-2-ene-2-yl)-6-oxohexanoate as salt of trifluoroacetic acid (16)

A solution of 25 mg (0.055 mmol) of the N-hydroxysuccinimidyl ester 15 in 1 mL of a 1:1 mixture of CF$_3$CO$_2$H:CH$_2$Cl$_2$ was stirred at room temperature under N$_2$ atmosphere for 1 hour. The solvent and excess of CF$_3$CO$_2$H were evaporated at reduced pressure in order to provide the salt with the trifluoroacetic acid of the active ester NHS-ANA-2 (16) as a colorless oil (24.4 mg, 96%). $^1$H NMR (300 MHz, THF-$d_8$) 7.26 (1H, dd, J=8.0, 3.7 Hz, H-3'), 5.13 (1H, apparent d, J=9.2 Hz, H-1'), 4.30 (1H, m, H-6'), 2.75 (4H, s broad, COCH$_2$CH$_2$CO), 2.75-2.70 (2H, m, H-5), 2.64-2.59 (4H, m, H-4'), 2.51-2.40 (2H, m, H-8'), 2.36-2.27 (1H, m, H-7'), 2.10 (1H, m, H-5'), 1.98 (1H, m, H-7'), 1.95-1.82 (3H, m, H-4, H-5'), 1.70 (2H, m, H-3), $^{19}$F NMR (282 MHz, THF-$d_8$) δ −76.86.

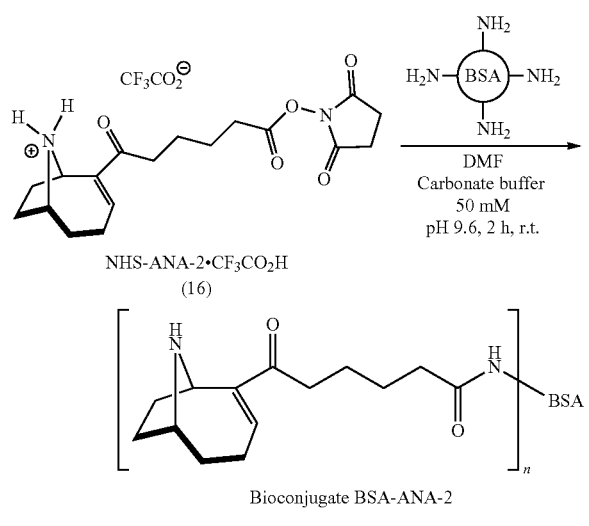

Bioconjugate BSA-ANA-2

2.2 Preparation of a Bioconjugate of the Hapten ANA-2 with BSA (BSA-ANA-2)

The conjugate was prepared as previously described for the bioconjugate BSA-ANA-1 from 200 µL of a 50 mM solution in DMF of the activated hapten NHS-ANA-2 (16) and 1.8 mL of a BSA solution (15 mg/mL) in 50 mM carbonate buffer, pH 9.6. After chromatographic purification, the collected fractions were brought to a final concentration of 1 mg/mL in elution buffer and were stored at −20° C. The number of molecules (16) conjugated to each BSA molecule as determined by MALDI-TOF-MS was n=14.5 (see Table 1, entry 3).

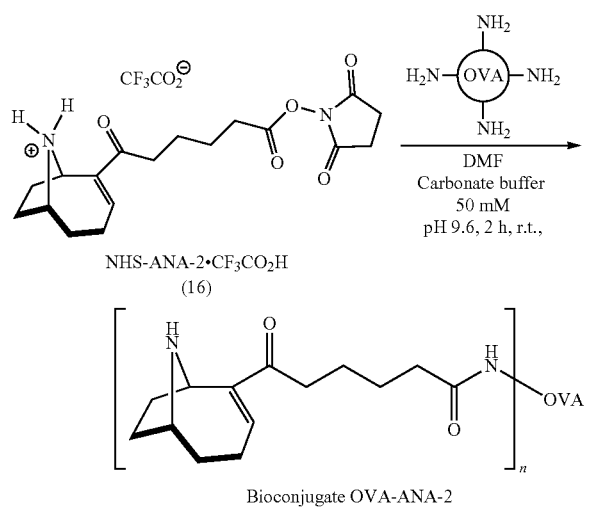

Bioconjugate OVA-ANA-2

2.3 Preparation of a Bioconjugate of the Hapten ANA-2 with OVA (OVA-ANA-2)

The conjugate was prepared as previously described for the bioconjugate OVA-ANA-1 from 100 µL of a solution of 50 mm in DMF of the activated hapten NHS-ANA-2 (16) and 1.9 mL of a OVA solution (15 mg/mL) in 50 mM carbonate buffer, pH 9.6. After the corresponding chromatographic purification, the collected fractions were brought to a final concentration of 1 mg/mL in elution buffer with 0.01% (v/v) thimerosal and were stored at −20° C. The number of molecules (16) conjugated to each OVA molecule as determined by MALDI-TOF-MS was n=8.4 (see Table 1, entry 7).

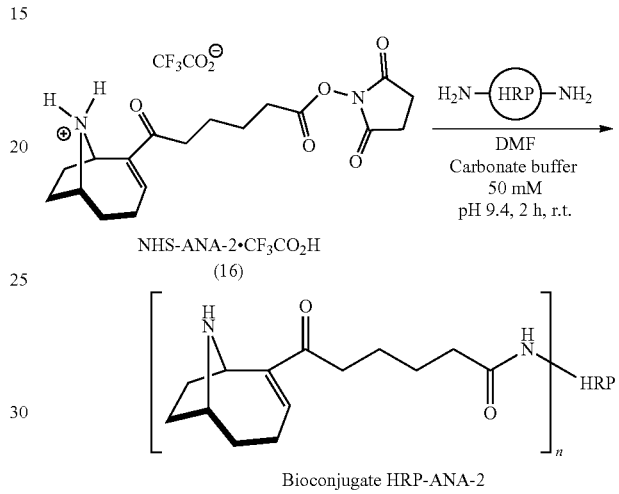

Bioconjugate HRP-ANA-2

2.4 Preparation of a Bioconjugate of the Hapten ANA-2 with HRP (HRP-ANA-2)

Prepared from 100 µL of a 5 mM solution of the activated hapten NHS-ANA-2 (16) in DMF and 0.9 mL of a HRP solution (2.5 mg/mL) in 50 mM carbonate buffer, pH 7.4. After the corresponding chromatographic purification, the fractions obtained containing the bioconjugate were brought to known concentrations of between 250-650 µg/mL in PBS buffer with 1% (w/v) BSA and 0.02% (w/v) thimerosal and were stored at 4° C. The number of molecules (16) conjugated to each HRP molecule as determined by MALDI-TOF-MS was n=4.1 (see Table 1, entry 11).

Example 3

Preparation of bioconjugates of formula (I) for T=R-III, L=═N—O—CH$_2$, Z=—(C═O)NH— and P=BSA, OVA and HRP.

3.1 Preparation of the Ester of n-Hydroxysuccinimidyl of the Hapten ANA-3 (NHS-ANA-3)

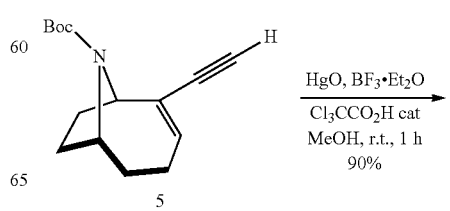

-continued

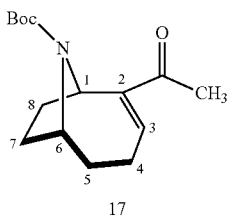

17

Preparation of tert-butyl 2-acetyl-9-azabicyclo[4.2.1]non-2-ene-9-carboxylate (17)

A solution prepared from 1 mg of trichloroacetic acid and 22 µL of BF$_3$·Et$_2$O in 1.9 mL of methanol, was added dropwise over a mixture prepared from 140 mg (0.569 mmol) of the alkyne 5 (0.283 mmol) and 0.5 equivalents of HgO (62 mg, 0.284 mmol) in 3.6 mL of MeOH anhydrous under inert atmosphere. The resulting reaction mixture was stirred for 1 hour at room temperature. After this time, 300 mL of distilled water was added to the reaction mixture and the stirring was continued for 15 additional minutes. Thereafter, the reaction mixture was poured over 10 mL of cold water and 5 mL of a saturated aqueous solution of NaHCO$_3$, extracted with CH$_2$Cl$_2$ (3×15 mL) and the collected organic phases were washed with brine, dried over Na$_2$SO$_4$ and concentrated at reduced pressure, providing a yellow oil. The purification by column chromatography using hexane-AcOEt 9:1 as the eluent provided N-Boc anatoxin-a (17) as a colorless oil (134 mg, 90%). IR $v_{max}$/cm$^{-1}$ 2978.5, 2925.8, 2853.6, 1690.6, 1662.9, 1404.7, 1390, 1363.2, 1337.5, 1231, 1168, 1108.1, 991.3; $^1$H NMR (300 MHz, CDCl$_3$) (mixture of 2 rotamers in a proportion of 3:1; the data of the majority are described) δ 6.81 (1H, m, H-3), 5.12 (1H, m, H-1), 4.44-4.23 (1H, m, H-6), 2.52-2.43 (2H, m, H-4), 2.29 (3H, s, Me), 2.22-2.0 (3H, m, H-8, H-7), 1.69-160 (3H, m, H-5, H-7), 1.37 (9H, s, CMe$_3$); $^{13}$C NMR (75 MHz, CDCl$_3$) δ 197.9 (COMe), 150.5 (C=O Boc), 142.2 (C-2), 141.4 (C-3), 79.5 (CMe$_3$ Boc), 55.8 (C-6), 53.2 (C-1), 31.6 (C-8), 30.5 (C-7), 29.1 (C-5), 28.9 and 28.6 (CMe$_3$ Boc). 25.5 (Me), 24.3 (C-4); EMAR (ES) m/z calculated for C$_{15}$H$_{24}$NO$_3$ [M+H]$^+$ 266.1751, found 266.1747.

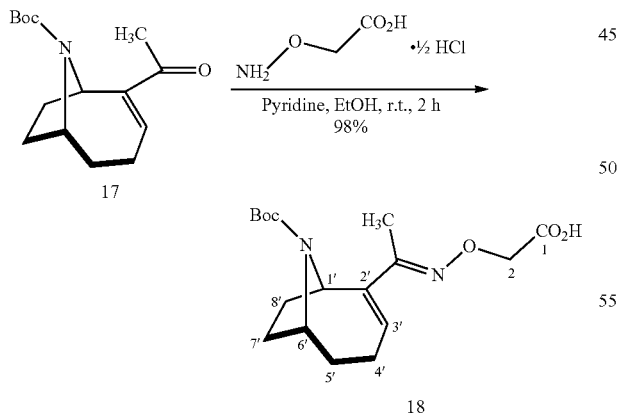

Preparation of 2-((((E)-1-(-9-(tert-butoxycarbonyl)-9-azabicyclo[4.2.1]non-2-ene-2-yl)ethylidene)amine)oxy)acetic acid (18)

46 µL of pyridine was added to a solution of 50 mg (0.178 mmol) of N-Boc anatoxin-a (17) and 3.0 equivalents (0.534 mmol) of aminooxyacetic acid hydrochloride in 3.2 mL of dry ethanol under argon atmosphere. The mixture was stirred at room temperature until the consumption of all the starting material was confirmed (2 hours) by CCF (using CHCl$_3$—CH$_3$CO$_2$H-MeOH, 92:4:4 as the eluent). The reaction mixture was poured over a mixture of 15 mL of ice water and 10 mL of 1 M HCl, extracted with CHCl$_3$ (4×10 mL) and the organic phases were washed with brine and were dried over Na$_2$SO$_4$ anhydrous. The evaporation of the solvent at reduced pressure provided a slightly yellow oil corresponding to the oxime 18 (59 mg, 98%) which appeared to be nearly pure by NMR analysis, so further purification was not required. IR $v_{max}$/cm$^{-1}$ 2972.6, 2929.2, 2539.5, 1739.9, 1674.0, 1593.5, 1476.5, 1408.4, 1364, 1336.8, 1257.2, 1168.8, 1,109.8, 1066.4; $^1$H NMR (300 MHz, CDCl$_3$) (mixture of 2 rotamers in a proportion of 3:1; the data of the majority are described) δ 6.07 (1H, m, H-3'), 5.15 (1H, m, H-1'), 4.66 (2H, m, H-2), 4.36 (1H, m, H-6'), 2.39-2.25 (2H, m, H-4'), 2.22-2.12 (3H, m, H-7', H-8'), 2.01 (3H, s, Me-C=N), 1.78-1.51 (3H, m, H-5', H-7'), 1.38 (9H, s, CMe$_3$ Boc) $^{13}$C NMR (75 MHz, CDCl$_3$) δ 172.9 (C-1), 157.7 (C=NO), 153.7 (CO$_2$ Boc), 144.9 (C-2'), 132.1 (C-3'), 79.1 (CMe$_3$ Boc), 68.6 (C-2), 55.5 (C-6'), 55.2 (C-1'), 34.3 (C-8'), 31.5 (C-7'), 28.6 (CMe$_3$ Boc), 24.2 (C-4'), 11.3 (Me-C=N); EMAR (ES) m/z calculated for C$_{17}$H$_{27}$N$_2$O$_5$ [M+H]$^+$ 339.1914, found 339.1912.

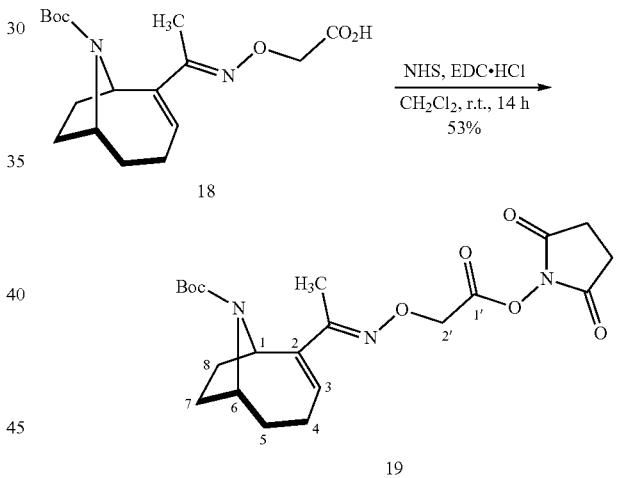

Preparation of tert-butyl 2-((E)-1-((2-((-1-yl)oxy-2-oxoethoxy)imine)ethyl-9-azabicyclo[4.2.1]non-2-ene-9-carboxylate (19)

A solution of 86.6 mg (0.256 mmol) of the acid 18, 1.5 equivalents (44.2 mg, 0.384 mmol) of N-hydroxysuccinimide and 1.5 equivalents (73.6 mg, 0.384 mmol) of EDC HCl in 6.0 mL of dry CH$_2$Cl$_2$ was stirred at room temperature under N$_2$ atmosphere and the progress of the reaction was controlled by CCF, using acetone-chloroform 9:1 as the eluent. After 17 hours, the complete disappearance of the starting material was confirmed, and the reaction mixture was diluted with CH$_2$Cl$_2$. Then, 2 mL of a saturated solution of NH$_4$Cl was added and extracted with the same solvent (3×10 mL). The collected organic phases were washed with brine and were dried over Na$_2$SO$_4$ anhydrous. After evaporating the solvent in vacuum, a colorless oil was obtained which was purified by column chromatography using CHCl$_3$ as the eluent, obtaining the N-hydroxysuccinimidyl ester 19 (59 mg, 53%). IR $v_{max}$/cm$^{-1}$ 2973, 2928.6, 1826.7, 1787.8, 1737.8, 1682.6, 1407.4, 1363.4, 1199.6, 1169.3, 1109.8, 1071.4, 861, 750.7; $^1$H NMR (300 MHz, CDCl$_3$) (a mixture of 2 rotamers in a proportion of 2:1; the data of the majority are described) δ 6.05 (1H, ddd, J=6.1, 6.1, 0.5 Hz, H-3), 5.15 (1H, m, H-1), 4.97 (2H, m, H-2'), 4.31 (1H, m, H-6), 2.84 (4H, s broad, COCH$_2$CH$_2$CO), 2.37-2.20 (3H, m, H$_2$-4 and H-8), 2.20-2.03 (2H, m, H-5 and H-7), 2.00 (3H, s, Me), 1.80-1.55 (3H, m, H'-8, H'-7 and H'-5), 1.37 (9H, s, Me$_3$C-Boc); $^{13}$C NMR (75 MHz, CDCl$_3$) δ 168.8 (COCH$_2$CH$_2$CO), 165.5 (C-1'), 157.7 (C=NO), 153.7 (CO$_2$-Boc), 144.9 (C-2), 132.1 (C-3), 79.1 (Me$_3$C-Boc), 68.6 (C-2'), 55.5 (C-6), 55.2 (C-1), 31.9 (C-5), 31.5 (C-8), 29.8 (C-7), 28.6 (Me$_3$C-Boc), 25.7 (COCH$_2$CH$_2$CO), 24.2 (C-4), 11.3 (Me); EMAR (ES) m/z calculated for C$_{21}$H$_{30}$N$_3$O$_7$ [M+H]$^+$ 436.2078 found 436.2083.

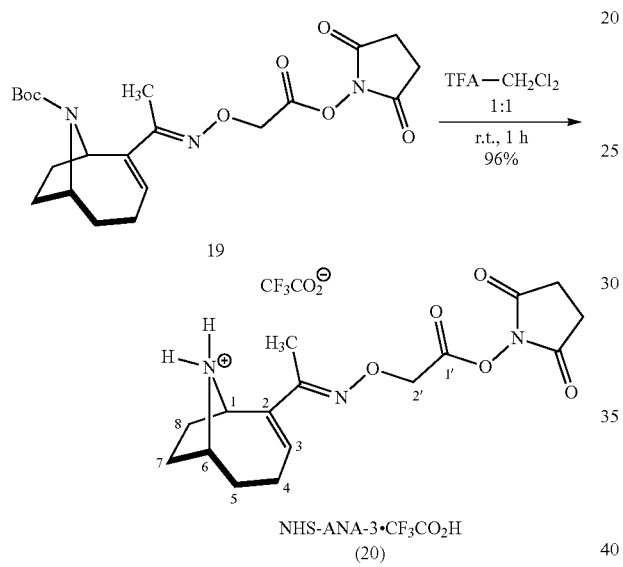

Preparation of 2,5-dioxopyrrolidin-1-yl 2-((((E)-1-(-9-azabicyclo[4.2.1]non-2-ene-2-yl)ethylidene)amino)oxy)acetate as the salt of trifluoroacetic acid (NHS-ANA-3, 20)

A solution of 28.0 mg (0.064 mmol) of the N-hydroxysuccinimidyl ester 19 in 1 mL of a 1:1 mixture of CF$_3$CO$_2$H:CH$_2$Cl$_2$ was stirred for 1 hour at room temperature under N$_2$ atmosphere. The course of the reaction was monitored by CFF using acetone-chloroform 8:2 as the eluent in order to check the absence of the starting material. When the reaction concluded, the solvent and the excess of CF$_3$CO$_2$H were evaporated at reduced pressure and a colorless oil corresponding to the activated ester NHS-ANA-3 as the salt of trifluoroacetic acid (20) was obtained (27.7 mg, 96%). IR $v_{max}$/cm$^{-1}$ 2948.1, 2359.6, 1783.8, 1737.4 f, 1705.2, 1668.8, 1429.5, 1191.0, 1132.7, 1074.1, 720.1; $^1$H NMR (300 MHz, CDCl$_3$) δ 6.45 (1H, ddd, J=6.0, 6.0, 0.5 Hz, H-3), 5.43 (1H, m, H-1), 4.92 (2H, apparent s broad, H-2'), 4.37 (1H, m, H-6), 2.82 (4H, s broad, COCH$_2$CH$_2$CO), 2.56 (3H, m, H$_2$-4 and H-8), 2.34 (1H, m, H-5), 2-06-1.98 (3H, m, H'-5 and H-7), 2.01 (3H, s, Me), 1.88 (1H, m, H'-7); $^{13}$C NMR (75 MHz, CDCl$_3$) δ 169.4 (COCH$_2$CH$_2$CO), 165.3 (C-1'), 156.6 (C=NO), 140.3 (C-2), 136.3 (C-3), 69.4 (C-2'), 59.6 (C-6), 54.4 (C-1), 30.1 (C-8), 28.8 (C-7), 27.9 (C-5), 25.1 (COCH$_2$CH$_2$CO), 23.3 (C-4), 10.8 (Me); $^{19}$F NMR (282 MHz, CDCl$_3$) δ −76.34 (s); EMAR (ES) m/z calculated for C$_{16}$H$_{22}$N$_3$O$_5$ [M+H]$^+$ 336.1554, found 336.1565.

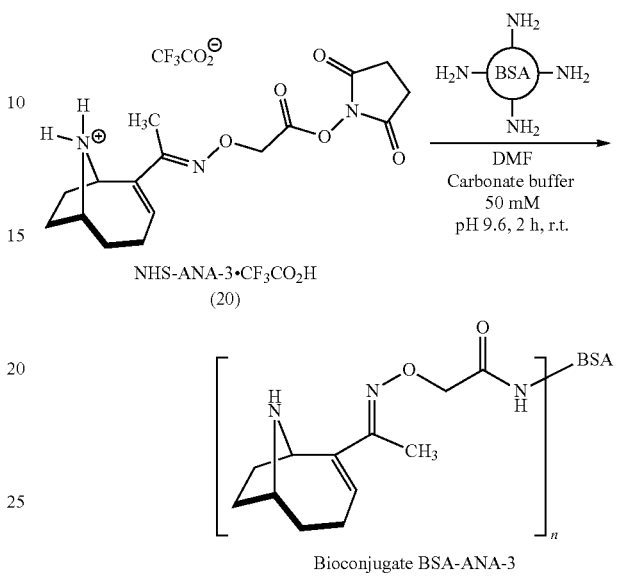

3.2 Preparation of a Bioconjugate of the Hapten ANA-3 with BSA (BSA-ANA-3)

Prepared as has been previously described for the bioconjugate BSA-ANA-1 from 200 μl of a solution of 50 mm in DMF of the activated hapten NHS-ANA-3 (20) and 1.8 ml of a BSA solution (15 mg/ml) in carbonate buffer 50 mm, pH 9.6. After the corresponding chromatographic purification, the collected fractions were brought to a final concentration of 1 mg/mL in elution buffer and were stored at −20° C. The number of molecules of 20 conjugated to each BSA molecule as determined by MALDI-TOF-MS was n=16 (see Table 1, entry 4).

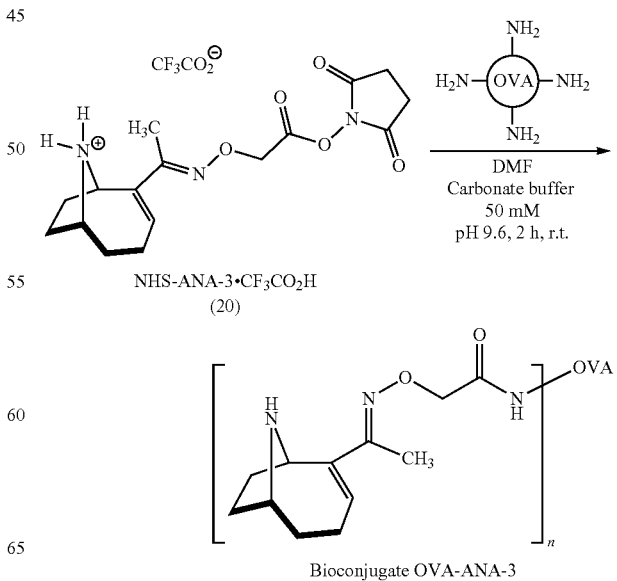

3.3 Preparation of a Bioconjugate of the Hapten ANA-3 with OVA (OVA-ANA-3)

The conjugate was prepared as previously described for the bioconjugate OVA-ANA-1 from 100 µL of a 50 mM solution in DMF of the activated hapten NHS-ANA-3 (20) and 1.9 mL of a OVA solution (15 mg/mL) in 50 mM carbonate buffer, pH 9.6. After chromatographic purification, the collected fractions were brought to a final concentration of 1 mg/mL in elution buffer with 0.01% (v/v) of thimerosal and were stored at −20° C. The number of molecules of 20 conjugated to each OVA molecule as determined by MALDI-TOF-MS was n=7.9 (see Table 1, entry 8).

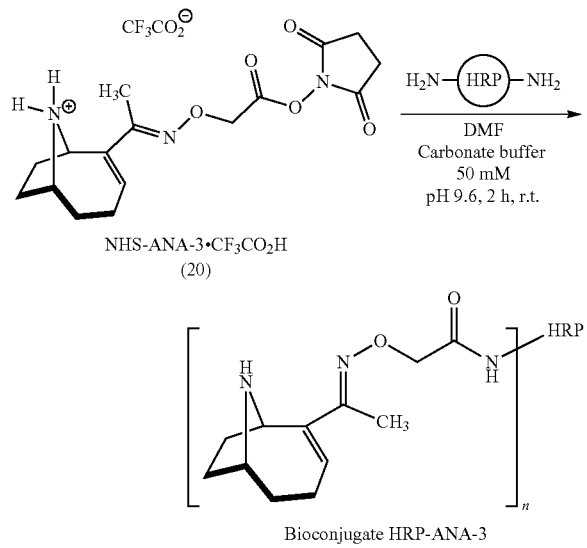

3.4 Preparation of a Bioconjugate of the Hapten ANA-3 with HRP (HRP-ANA-3)

Prepared from 100 µL of a 5 mM solution of the activated hapten NHS-ANA-3 (20) in DMF and 0.9 mL of a HRP solution (2.5 mg/mL) in 50 mM carbonate buffer, pH 7.4. After chromatographic purification, the fractions obtained containing the bioconjugate were brought to known concentrations of between 250-650 µg/mL in PBS buffer with 1% (w/v) BSA and 0.02% (w/v) thimerosal and were stored at 4° C. The number of molecules of 20 conjugated to each HRP molecule as determined by MALDI-TOF-MS was n=2.5 (see Table 1, entry 12).

2. ELISA Method 96-well polystyrene plates were used. Each antibody was evaluated in the two classic competitive ELISA formats (the immobilized antigen or conjugate with indirect detection format and the immobilized antibody with direct detection format) using homologous assay antigens, that is to say, an assay antigen from the same bioconjugate of formula (I) as the one used for obtaining the immunogen, but in which P=OVA or HRP. After each incubation step, the plates were washed four times with a washing solution, using a ELx405 96-channel washer (Biotek Instruments, Winooski, USA). The signal produced by the peroxidase used as a label was revealed with 100 µL per well of a 2 mg/mL solution of o-phenylenediamine in 25 mM citrate, 62 mM phosphate, pH 5.4, containing 0.012% (v/v) of $H_2O_2$. The enzymatic reaction was performed for 10 minutes at room temperature and was stopped using 100 µL per well of 2.5 M sulfuric acid. Upon concluding the assays, the absorbance of each well was read at 492 nm using a reference wavelength at 650 nm in a PowerWave HT microplate reader (Biotek Instruments, Winooski, USA). The sigmoid standard curves obtained when representing the absorbance versus the analyte concentration were adjusted to a four-parameter logistic equation using the SigmaPlot computer package from SPSS (Chicago, USA).

The affinity of the antibody ($IC_{50}$) was estimated as the concentration of free analyte capable of reducing the maximum signal ($A_{max}$) to half.

2.1 Competitive ELISA Tests in the Immobilized Antigen or Conjugate Format with Indirect Detection (Indirect Assay)

The plates were coated with 100 µL per well of an assay antigen solution which is a bioconjugate of formula (I) where P is OVA, at 0.01 or at 0.1 µg/mL in 50 mM carbonate buffer, pH 9.6, by overnight incubation at room temperature. After washing the plates, 50 µL per well of a complete standard curve of the analyte in PBS was dispensed in each column, followed by 50 µL per well of antibody diluted in PBST (0.05% Tween 20). The immunochemical reaction was carried out for 1 hour at room temperature and then the plates were washed. Subsequently, each well received 100 µL of a 1/2000 RAM-HRP dilution (rabbit anti-mouse immunoglobulins labeled with peroxidase) in PBST. This reaction was left at room temperature for 1 hour. After washing the plates, the retained peroxidase activity was revealed and the absorbance was read at 492 nm as previously described.

2.2. Competitive ELISA Tests in the Immobilized Antibody Format with Direct Detection (Direct Assay)

The plates were coated with 100 µL per well of an antibody solution in 50 mM carbonate buffer, pH 9.6 by overnight incubation at room temperature. After washing the plates, 50 µL per well of a complete standard curve of the analyte in PBS was dispensed in each column, followed by 50 µL per well of a specific dilution in PBST of the enzymatic bioconjugate which is a bioconjugate of formula (I) where P is HRP.

The same reagent distribution was repeated for each plate with a different antibody. The immunochemical reaction was carried out for 1 hour at room temperature and the plates were then washed. Lastly, the retained peroxidase activity was revealed and the absorbance was read at 492 nm as previously described.

3. Production of Mouse Monoclonal Antibodies

3.1 Mouse Immunization

For the immunization, the bioconjugates of formula (I) in which P is BSA (immunizing conjugates) obtained in the previous examples were used. BALB/c female mice, aged between 6 and 8 weeks at the start of the process, were employed.

In each dose, 100 µg of bioconjugate per mouse was administered via the intraperitoneal route, the total volume injected being 200 µL. In the first immunization, the bioconjugate was supplied as an emulsion prepared with Freund's Complete Adjuvant (1:1, v/v). At intervals of 3 weeks, the mice received two additional immunizations, in these cases, emulsifying the bioconjugates with Freund's Incomplete Adjuvant. Four days before each cellular fusion, the mouse selected received a final dose of 100 µg of the corresponding bioconjugate diluted in PBS.

3.2 Cellular Fusions for Hybridoma Generation

The fusions with immunized mice were carried out basically following previously described methodologies that are well established in the state of the art.

Immediately after slaughtering the mice, the spleen was removed and homogenized with the plunger of a sterile syringe. After erythrocytes were lysed by osmotic shock with 1 mL of cold lysis buffer for one minute, the lymphocytes were washed twice with cold complete medium (with serum) and filtered to remove blood clot.

The myeloma line P3-X63-Ag8.653 was cultivated the days prior to the fusion in DMEM-supplemented medium [2 mM L-alanine-L-glutamine, 1 mM non-essential amino acids, 25 µg/mL gentamicin, 10% (v/v) fetal bovine serum (FBS)], maintaining the cells in the exponential growth phase such that the day of the fusion there was a sufficient number of the same.

After two washes with medium without serum, both cellular populations were combined at a lymphocyte:myeloma ratio of 4:1. Then, the cells were centrifuged in order to carry out the cellular fusion immediately thereafter. To this end, the chemical fusing agent PEG 1500 (1 mL per spleen, 1 minute) was used which, upon partially dissolving the membranes, allows for the fusion of the cells. Once both populations had been fused, the cells were resuspended in DMEM-supplemented medium [15% (v/v) FBS] and were seeded into 96-well culture plates (100 µL per well) at a cellular density of 150×10$^3$ lymphocytes per well and were incubated at 37° C. in an atmosphere with 5% of $CO_2$ and 95% humidity. 24 hours after the fusion, 100 µL per well of HAT medium was added for hybridoma selection [DMEM-supplemented with 100 µM hypoxanthine, 0.4 µM aminopterin, 16 µM thymidine and 20% (v/v) FBS which contained 1% (v/v) HFCS (high fusion and closing supplement)].

3.3. Selection, Cloning and Preservation of Hybridomas

Approximately 10-12 days after the cellular fusion, supernatant screening was carried out with the aim of identifying which one contained antibody-secreting hybridomas capable of recognizing anatoxin-a both in its conjugated and free form (competitor clones). Beforehand, the efficacy of the fusion was determined by visual inspection, defined as the percentage of wells which presented at least one clone that was clearly visible to the microscope.

In order to carry out the identification of competitor clones, supernatants were assayed by means of the differential ELISA technique consisting of analyzing in adjacent wells, in a parallel manner, each supernatant in the absence of analyte and in the presence of a prefixed analyte concentration, usually 100 nM. To this purpose, the plates were coated with the homologous conjugate which is a bioconjugate of formula (I) in which P is OVA at a concentration of 0.1 μg/mL and the test was carried out by adding 50 μL of the culture supernatant. The conditions for the indirect ELISA format, as detailed in section 2.1, were followed Thereafter, the wells containing antibody-producing hybridomas capable of providing an absorbance equal to or greater than 0.5 in the test in the absence of anatoxin-a and inhibiting the signal equal to or greater than 80% in the test in the presence of anatoxin-a were selected for further work. Additionally, for all the positive wells, a second more exhaustive screening was carried out in a bidimensional competitive manner with the aim of selecting the best hybridomas with greater certainty. To this end, the supernatant of each hybridoma was tested at 4 dilutions (1/8, 1/32, 1/128 and 1/512) in plates coated with the homologous bioconjugate at 0.01 and 0.1 μg/mL and using anatoxin-a as competitor at 5 and 50 nM. 200 μL of the culture supernatant was thus diluted in 600 μL of PBST and the following dilutions were serially made from this first dilution. The test was performed by adding 50 μLper well of the corresponding dilution of supernatant and 50 μL of the solution of anatoxin-a in PBS at the concentration of 100, 10 and 0 nM.

The cells into the wells ultimately selected were cloned by limiting dilution, seeding from each original well a new 96-well plate at 2 cells per well in HT medium (HAT medium without aminopterin and containing 1% (v/v) HFCS).

Usually 7-10 days after the first cell cloning, the wells which contained a unique cell clone were identified by means of visual inspection, and the culture supernatants were assayed as previously described for the screening of supernatants after cell fusion. This process was carried out as many times as it was necessary (at least twice) in order to ensure the monoclonality of the selected hybridomas as well as their stability. Lastly, the expansion of the selected cellular lines was carried out, progressively cultivating the hybridoma in containers of higher size. Once the clone had grown, the cells were frozen in liquid nitrogen at a concentration of $10^7$ cells per vial (2-4 vials for each hybridoma) in a FBS solution with 10% (v/v) DMSO as the cryoprotective agent. The vials were maintained at −80° C. in the interior of a polystyrene box for 24 hours before passing them to the liquid nitrogen container.

3.4 Production and Purification of Monoclonal Antibodies

In the last phase of the cellular expansion of the hybridomas, they were progressively divided into culture plates until a final volume of between 100 and 200 mL of supernatant was reached. The cells were left to grow until the confluence was reached and once the culture medium nutrients were depleted the content of the plates was collected. The collected volume was centrifuged in order to eliminate the cellular residues and the supernatant was precipitated by adding a volume of an ammonium sulfate saturated solution, being maintained at 4° C. until it was purified.

The purification of the antibodies was carried out by affinity chromatography with protein G columns following the manufacturer's instructions. To this end, the precipitated antibody was centrifuged for 20 minutes at 5000 rpm (4000×g) and the supernatant was discarded. The pellet which contained the antibodies was solubilized with 20 mM sodium phosphate buffer, pH 7.4 and filtered through nitrocellulose membranes (pore diameter 0.45 μm) to eliminate suspended solids. The elution of the antibody from the column was carried out with 100 mM sodium citrate buffer, pH 2.5. The fractions which contained the antibody were identified by means of UV spectrophotometry and were collected. The solution was neutralized by adding 1 M Tris-HCl, pH 9.5. Finally, the concentration of the purified antibody was determined by UV spectrophotometry [$A_{280\ (1\ mg/mL\ IgG)}$=1.4] and a working solution was prepared at a concentration of 500 μg/mL in PBS with 1% (w/v) BSA and 0.01% (w/v) thimerosal which was stored at 4° C. The remaining solution was precipitated with saturated ammonium sulfate [1:1, (v/v)] which guarantees its stability at 4° C. for years.

4. Results 4.1 Generation of Monoclonal Antibody-Producing Hybridomas Against Anatoxin-a Based on mice immunized with bioconjugates of formula (I), in which P is BSA, cellular fusions were carried out aimed at generating hybridomas. The bioconjugates of formula (I) in which T is R-I or R-III were not capable of inducing the generation of monoclonal antibody-secreting hybridomas with a high affinity towards anatoxin-a. On the other hand, based on the bioconjugate of formula (I) in which T is R-II, it was possible to obtain 5 monoclonal antibody-producing cellular lines with high affinity towards anatoxin-a. The monoclonal antibodies obtained from said hybridomas have been named for the purpose of the present invention and the examples included here: mAb #38, mAb #44, mAb #325, mAb #417 and mAb #39. This result reveals that the bioconjugate of formula (I) most suitable for obtaining antibodies to anatoxin-a is not a clear and obvious question. The results also demonstrate the suitability of a bioconjugate of formula (I) in which T is R-II for inducing the production of antibodies capable of recognizing anatoxin-a.

4.2 Determination of the Affinity of the Antibodies

Figures 6, 7:
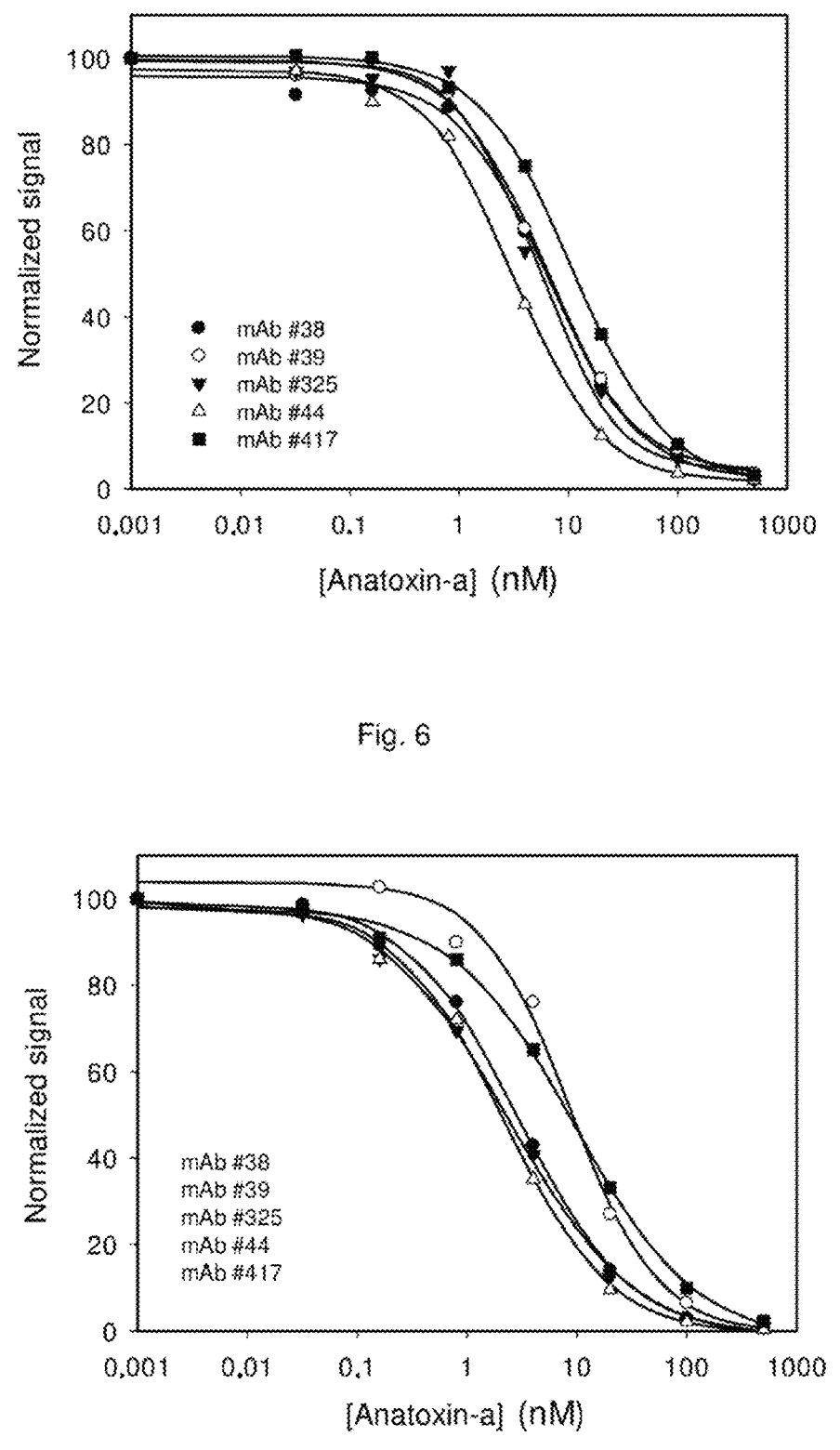

Once the 5 monoclonal antibodies obtained (see 4.1, antibodies mAb #38, mAb #44, mAb #325, mAb #417 and mAb #39) were purified, their affinity towards anatoxin-a was determined by means of homologous competitive ELISA. In the indirect format (FIG. 6), the antibodies exhibited $IC_{50}$ values for anatoxin-a ranging from 3.15 nM to 11.00 nM. In the direct format (FIG. 7), the antibodies exhibited $IC_{50}$ values for anatoxin-a ranging from 2.18 nM to 9.49 nm.

4.3. Determination of the Specificity of the Antibodies

Figure 8:
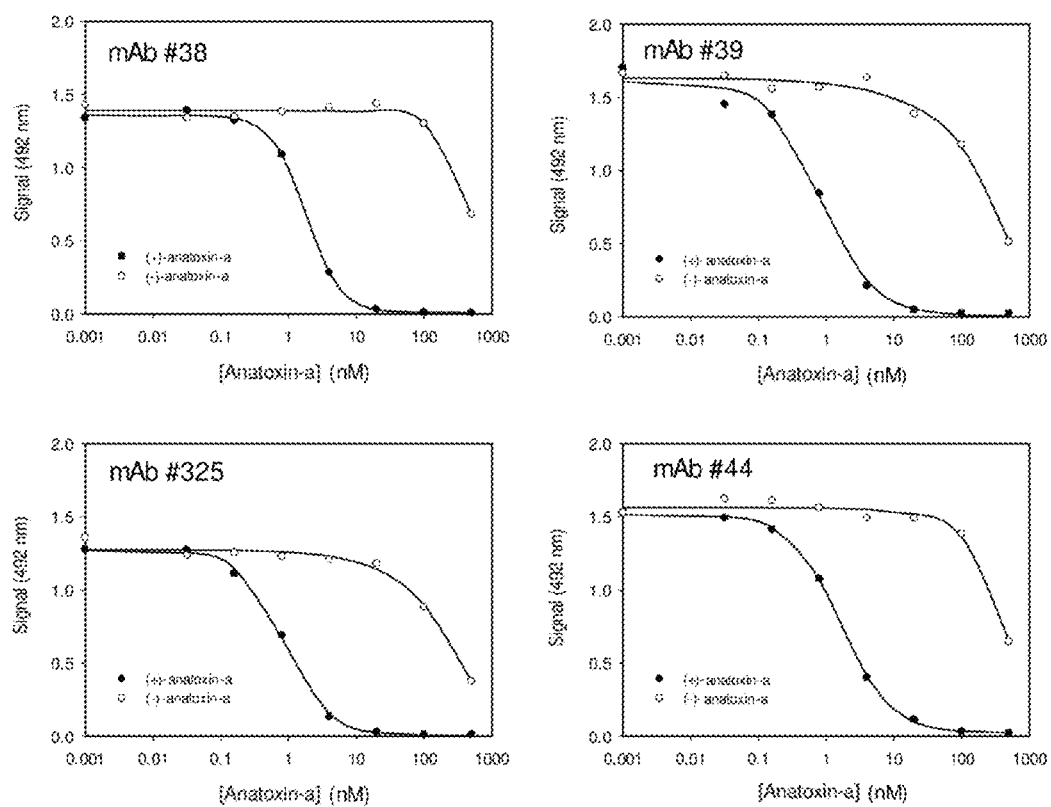

Anatoxin-a exists chemically in 2 enantiomeric forms. The natural cyanotoxin is exclusively dextrorotatory (+), while the levorotatory form (−) can be obtained by organic synthesis. In order to test the extent to which the obtained monoclonal antibodies were actually specific, they were tested in the homologous indirect ELISA format against the two enantiomers of anatoxin-a. As it may be observed in FIG. 8, all the antibodies recognized (+)-anatoxin-a with an affinity at least 100 times greater compared to the affinity they exhibited towards their enantiomer, (−)-anatoxin-a. This test convincingly demonstrates the significant specificity and discrimination ability of the monoclonal antibodies described in this invention and therefore their high capacity for determining the natural enantiomer of the anatoxin-a in samples, even in the presence of other potential contaminants.

The invention claimed is:

1. A bioconjugate of formula (Ib)

wherein P is bovine serum albumin and n is 14.5.

2. A method of producing a monoclonal antibody against anatoxin-a, the method comprising immunizing a mouse with the bioconjugate of claim 1.

* * * * *